United States Patent
Rehbein et al.

(10) Patent No.: US 11,241,542 B2
(45) Date of Patent: *Feb. 8, 2022

(54) SENSOR DEVICE REMOVABLY ATTACHABLE TO A DRUG DELIVERY DEVICE

(71) Applicant: Sanofi-Aventis Deutschland GMBH, Frankfurt am Main (DE)

(72) Inventors: Christian Rehbein, Frankfurt am Main (DE); Samuel Steel, Warwick (GB); Anthony Paul Morris, Warwick (GB); Matthew Meredith Jones, Warwick (GB); Robert Veasey, Warwick (GB); Richard James Vincent Avery, Warwick (GB); William Marsh, Warwick (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/823,694

(22) Filed: Mar. 19, 2020

(65) Prior Publication Data
US 2020/0222635 A1    Jul. 16, 2020

Related U.S. Application Data
(63) Continuation of application No. 16/060,859, filed as application No. PCT/EP2016/080504 on Dec. 9, 2016, now Pat. No. 10,625,022.

(30) Foreign Application Priority Data
Dec. 10, 2015 (EP) .................................. 15199195

(51) Int. Cl.
*A61M 5/315* (2006.01)
*A61M 5/24* (2006.01)
*A61M 5/31* (2006.01)

(52) U.S. Cl.
CPC .......... *A61M 5/31525* (2013.01); *A61M 5/24* (2013.01); *A61M 2005/3125* (2013.01);
(Continued)

(58) Field of Classification Search
None
See application file for complete search history.

(56) References Cited

U.S. PATENT DOCUMENTS 9,750,886 B2 * 9/2017 Plambech ........... A61M 5/1452
10,625,022 B2 * 4/2020 Rehbein ............ A61M 5/31525
(Continued)

FOREIGN PATENT DOCUMENTS

| CN | 102458514 | 5/2012 |
|---|---|---|
| CN | 102510762 | 6/2012 |

(Continued)

OTHER PUBLICATIONS

International Search Report and Written Opinion in International Application No. PCT/EP2016/080504, dated Jun. 12, 2018, 10 pages.
(Continued)

*Primary Examiner* — Shawn Decenzo
(74) *Attorney, Agent, or Firm* — Fish & Richardson P.C.

(57) ABSTRACT

A sensor device removably attachable to a drug delivery device includes a sensing arrangement arranged within the sensor device and circuitry configured to process signals provided by the sensing arrangement. The sensing arrangement is configured such that, when the sensor device is attached to the drug delivery device, the sensing arrangement is operable to read encoded information present on a
(Continued)

rotatable component internal to the drug delivery device and that is able to be sensed through a window or aperture of the drug delivery device, and is operable to sense through the window or aperture at least a part of a drive mechanism of the drug delivery device. The circuitry is configured to determine information relating to a set dose, and to determine information relating to whether the drug delivery device is in a dose setting mode or whether the device is in a dose delivery mode.

20 Claims, 18 Drawing Sheets

(52) U.S. Cl.
CPC .............. *A61M 2005/3126* (2013.01); *A61M 2205/3306* (2013.01); *A61M 2205/50* (2013.01); *A61M 2205/6063* (2013.01)

(56) References Cited

U.S. PATENT DOCUMENTS

| | | | |
|---|---|---|---|
| 2009/0299279 A1 | 12/2009 | Richter | |
| 2011/0160652 A1* | 6/2011 | Yodfat | A61M 5/14248 604/66 |
| 2011/0270214 A1* | 11/2011 | Jorgensen | A61M 5/31551 604/500 |
| 2013/0030409 A1* | 1/2013 | Macdonald | A61M 5/31578 604/506 |
| 2013/0033860 A1 | 2/2013 | Tong | |
| 2013/0338601 A1* | 12/2013 | Cowe | A61M 5/2033 604/189 |
| 2014/0354998 A1 | 12/2014 | Bock et al. | |
| 2015/0202375 A1* | 7/2015 | Schabbach | A61M 5/24 604/207 |
| 2016/0067417 A1* | 3/2016 | Bayer | A61M 5/31548 604/208 |
| 2017/0326301 A1* | 11/2017 | Butler | A61M 5/31536 |
| 2017/0368263 A1* | 12/2017 | Ploch | A61M 5/3158 |
| 2018/0200457 A1* | 7/2018 | Azeley | A61M 5/20 |
| 2018/0333330 A1* | 11/2018 | Nagar | F25D 3/08 |
| 2019/0117900 A1* | 4/2019 | Larsen | A61M 5/31583 |

FOREIGN PATENT DOCUMENTS

| | | |
|---|---|---|
| CN | 103957964 | 7/2014 |
| CN | 104203315 | 12/2014 |
| CN | 104519931 | 4/2015 |
| CN | 104902944 | 9/2015 |
| CN | 104936640 | 9/2015 |
| CN | 105073165 | 11/2015 |
| CN | 105102031 | 11/2015 |
| JP | 2010-505475 | 2/2010 |
| JP | 2013-505433 | 2/2013 |
| JP | 2015-509770 | 4/2015 |
| JP | 2016-502899 | 2/2016 |
| JP | 2016-514599 | 5/2016 |
| JP | 2016-515454 | 5/2016 |
| JP | 2016-529050 | 9/2016 |
| WO | WO 2008/145171 | 12/2008 |
| WO | WO 2010/142598 | 12/2010 |
| WO | WO 2011/007212 | 1/2011 |
| WO | WO 2011/032960 | 3/2011 |
| WO | WO 2011/036133 | 3/2011 |
| WO | WO 2011/039212 | 4/2011 |
| WO | WO 2011/117212 | 9/2011 |
| WO | WO 2013/004843 | 1/2013 |
| WO | WO 2013/083715 | 6/2013 |
| WO | WO 2013/110538 | 8/2013 |
| WO | WO 2013/120776 | 8/2013 |
| WO | WO 2013/120778 | 8/2013 |
| WO | WO 2014/023763 | 2/2014 |
| WO | WO 2014/036346 | 3/2014 |
| WO | WO 2014/111340 | 7/2014 |
| WO | WO 2014/111341 | 7/2014 |
| WO | WO 2014/111342 | 7/2014 |
| WO | WO 2014/128157 | 8/2014 |
| WO | WO 2014/166907 | 10/2014 |
| WO | WO 2014/166911 | 10/2014 |
| WO | WO 2014/173434 | 10/2014 |
| WO | WO 2014/173768 | 10/2014 |
| WO | WO 2014/173775 | 10/2014 |
| WO | WO 2014/198798 | 12/2014 |
| WO | WO 2015/036346 | 12/2014 |

OTHER PUBLICATIONS

International Preliminary Report on Patentability in International Application No. PCT/EP2016/080504, dated Feb. 27, 2017, 13 pages.

* cited by examiner

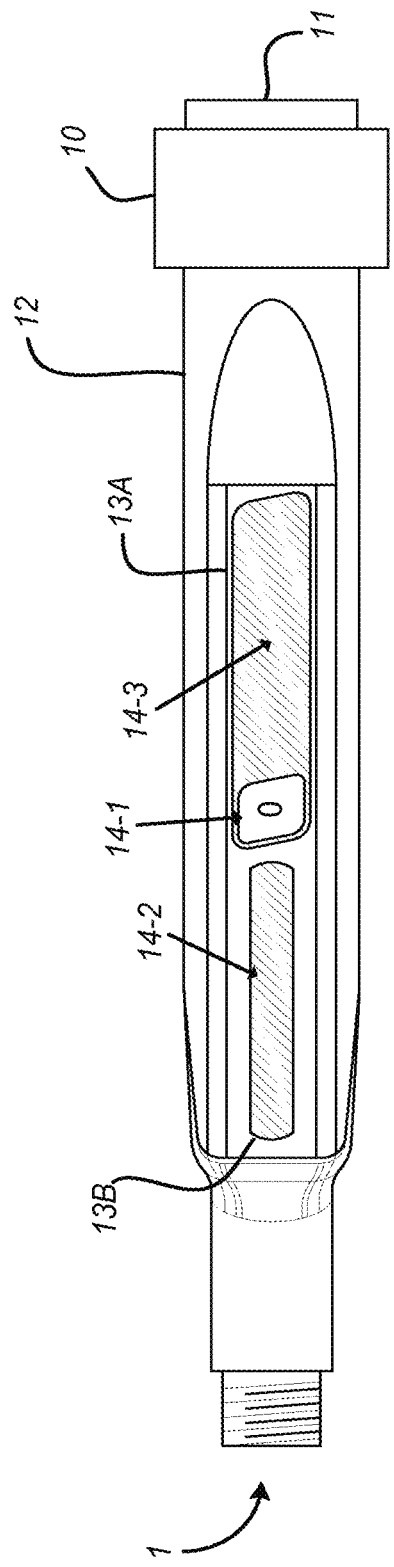
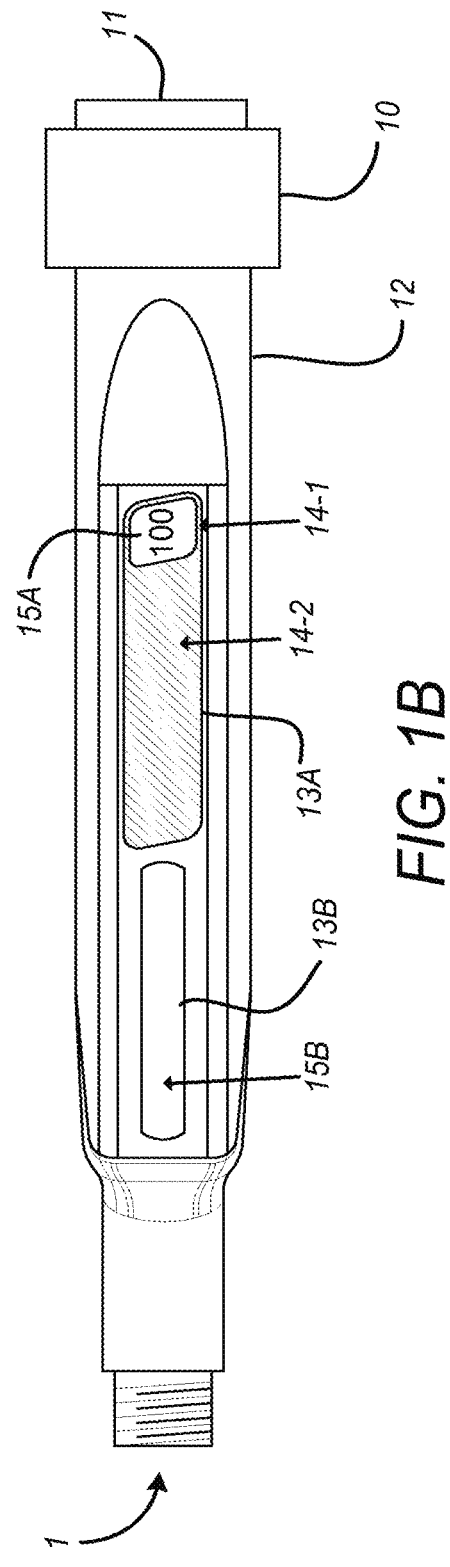
FIG. 1A
FIG. 1B

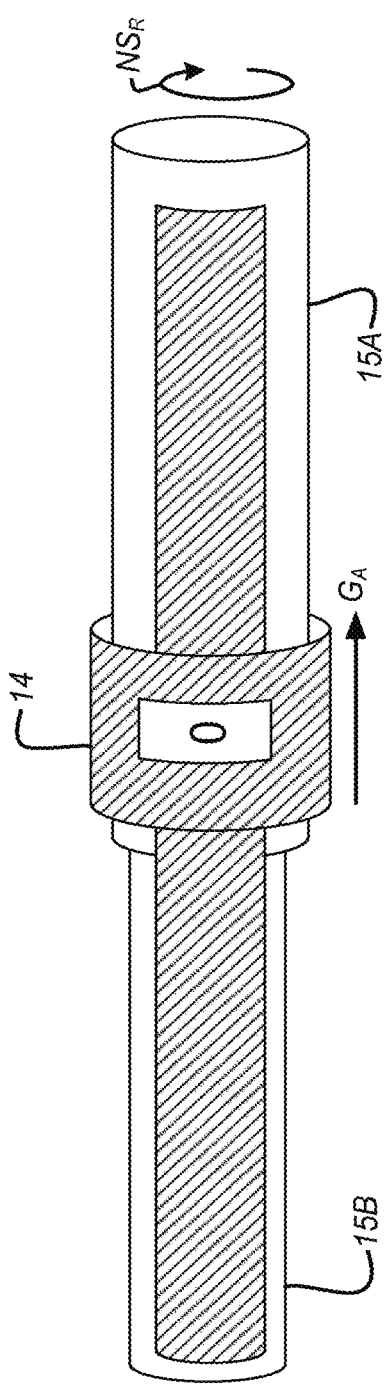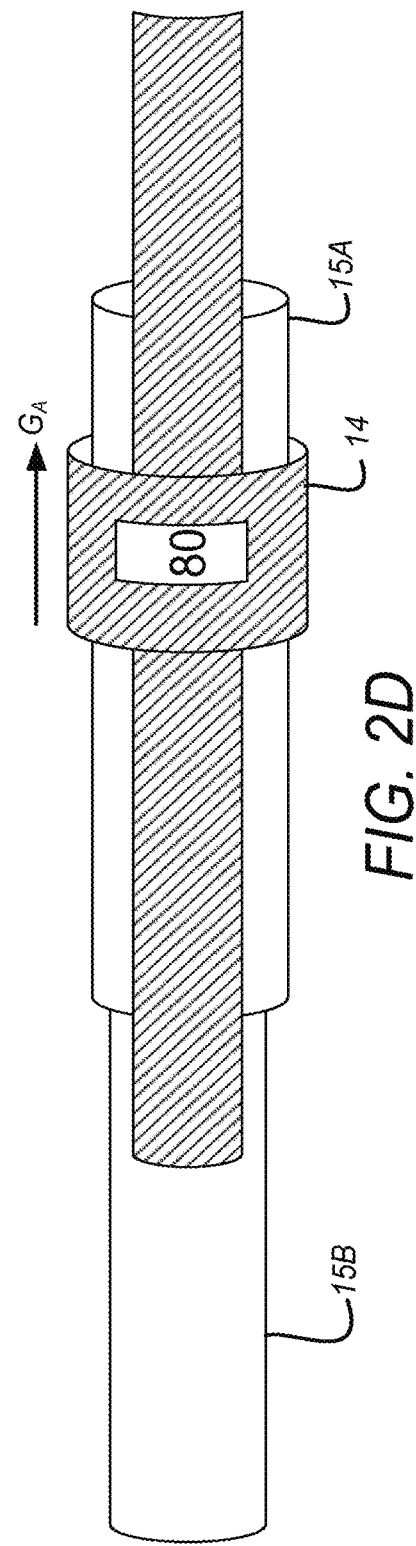

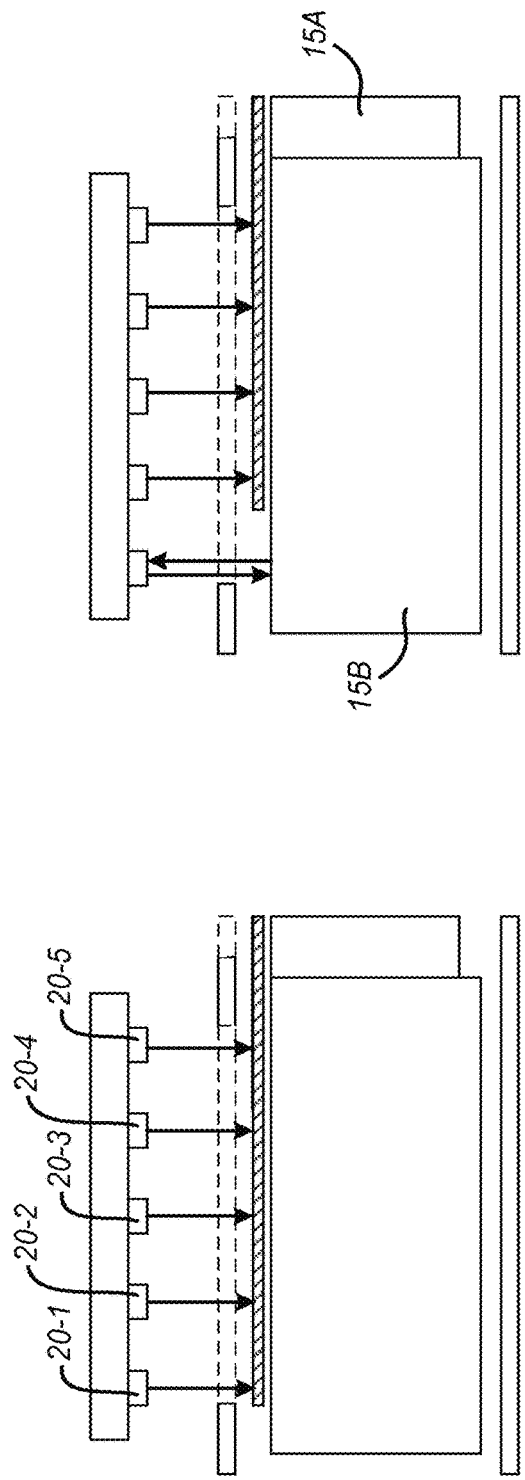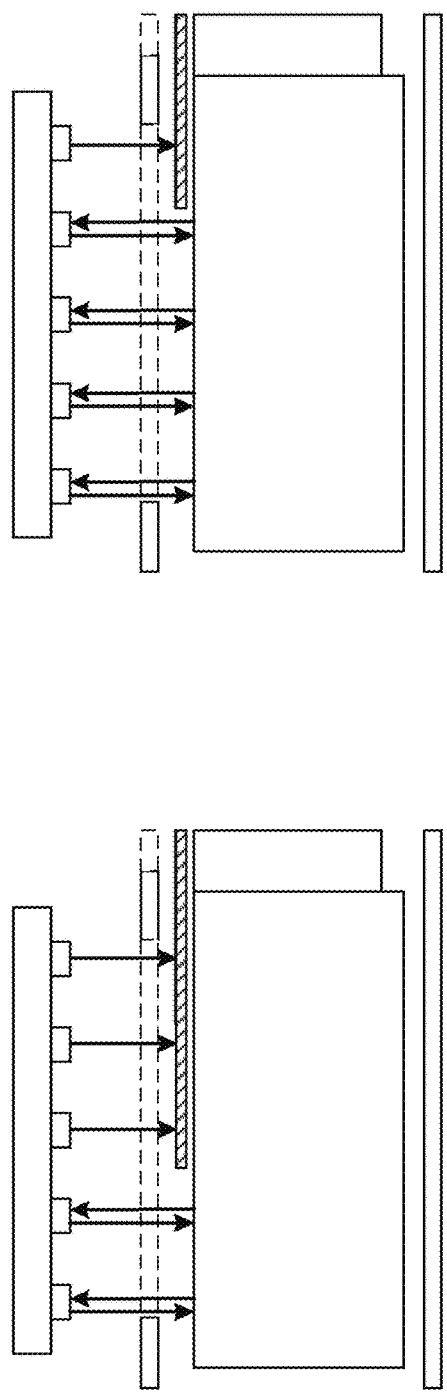



SENSOR DEVICE REMOVABLY ATTACHABLE TO A DRUG DELIVERY DEVICE

CROSS REFERENCE TO RELATED APPLICATIONS

The present application is a continuation of U.S. patent application Ser. No. 16/060,859, filed on Jun. 8, 2018, which is the national stage entry of International Patent Application No. PCT/EP2016/080504, filed on Dec. 9, 2016, and claims priority to Application No. EP 15199195.7, filed on Dec. 10, 2015, the disclosures of which are expressly incorporated herein in entirety by reference thereto.

TECHNICAL FIELD

The invention relates to a sensor device removably attachable to a drug delivery device such as an injection pen.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning (dialling) a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose.

It has been described, for instance in WO 2011/117212, to provide a supplementary device comprising a mating unit for releasably attaching the device to an injection/drug delivery device. The device includes a camera and is configured to perform optical character recognition (OCR) on captured images visible through a dosage window of the injection pen, thereby to determine a dose of medicament that has been dialled into the injection device. In order for such a supplementary device to successfully determine the dose, the dosage window must remain stationary. However not all drug delivery devices operate in this way.

SUMMARY

According to a first aspect of the disclosure there is provided a sensor device removably attachable to a drug delivery device, the sensor device comprising:

a sensing arrangement arranged within the sensor device; and circuitry configured to process signals provided by the sensor arrangement, wherein the sensing arrangement is configured such that, when the sensor device is attached to the drug delivery device, the sensing arrangement is operable to read encoded information present on a rotatable component that is internal to the drug delivery device and that is able to be sensed through a window or aperture of the drug delivery device, and is operable to sense through the window or aperture at least a part of a drive mechanism of the drug delivery device, wherein the circuitry is configured:

to determine, based on the encoded information, information relating to a set dose, and to determine, based on sensing of the part of the drive mechanism, information relating to whether the drug delivery device is in a dose setting mode or whether the device is in a dose delivery mode.

The sensing arrangement may be is an optical sensor arrangement, for instance a single camera.

The sensing arrangement may comprise a light source arrangement configured to project light towards the aperture or window in the drug delivery device when the sensor device is attached to the drug delivery device.

The sensor device may further comprise a second sensing arrangement arranged within the sensor device and configured to detect an amount of axial movement of a gauge element of the drug delivery device, and wherein the circuitry is configured to calculate a set dose using the encoded information and using outputs from the second sensing arrangement. The second sensing arrangement may comprise an array of optical sensors, each optical sensor being operable to detect light received at different locations along the linear path and to output a signal indicative of an amount of detected light.

The second sensing arrangement may be configured to determine an angular position of a mark on the gauge element.

The sensor arrangement may be configured to determine a drug for which the drug delivery device is being used to dispense using the encoded information or using outputs from the second sensing arrangement.

A second aspect of the disclosure provides a drug delivery system comprising:

the sensor device described above; and the drug delivery device having the window or aperture.

The part of the drive mechanism may be of a contrasting colour to the rotatable component.

The drug delivery device may comprise the gauge element that is moveable axially along an underlying element and is configured such that movement of the first movable element in a particular direction causes the underlying element to become visible at successive locations along the externally visible path, wherein at least part of the gauge element has a first reflectance and the underlying element has a second, different reflectance.

The first moveable element may be movable relative to the underlying element such that movement in a first direction along the externally visible path causes an increasing length of the underlying element to become visible in the externally visible path.

The drug delivery device may comprise the gauge element that is moveable axially along the device, wherein the gauge element has formed thereon marks that are at different angular positions at different axial positions.

A third aspect of the disclosure provides a drug delivery device comprising:

a main body;

a number sleeve having markings thereon;

a dose setting mechanism configured to rotate the number sleeve with axially moving the number sleeve as a dose set is increased or decreased in a dose setting mode;

a drive mechanism configured to cause expulsion of a set dose upon application of a driving force in a dose delivery mode;

a window located at a fixed axial position on the main body and coincident with the markings on the number sleeve, wherein at least a part of the drive mechanism is coincident with the window and is visible through the window when the injection device is in the dose delivery mode and is not visible through the window when the injection device is in the dose setting mode. The part of the drive mechanism may be a drive sleeve.

BRIEF DESCRIPTION OF THE FIGURES

For a more complete understanding of example embodiments of the present disclosure, reference is now made to the following description taken in connection with the following Figures, in which:

FIGS. 1A and 1B shows views of a drug delivery device with which a sensor device according to various embodiments may be used;

FIGS. 2A to 2E are illustrative simplified views of various components, and combinations of components, of a drug delivery device such as that of FIGS. 1A to 1D with which a sensor device according to various embodiments may be used;

FIGS. 4A to 4D show various views of the drug delivery device and the sensor array of the sensor device of FIG. 3 for the purpose of illustrating the operation of the sensor device;

DETAILED DESCRIPTION

Figure 1C:
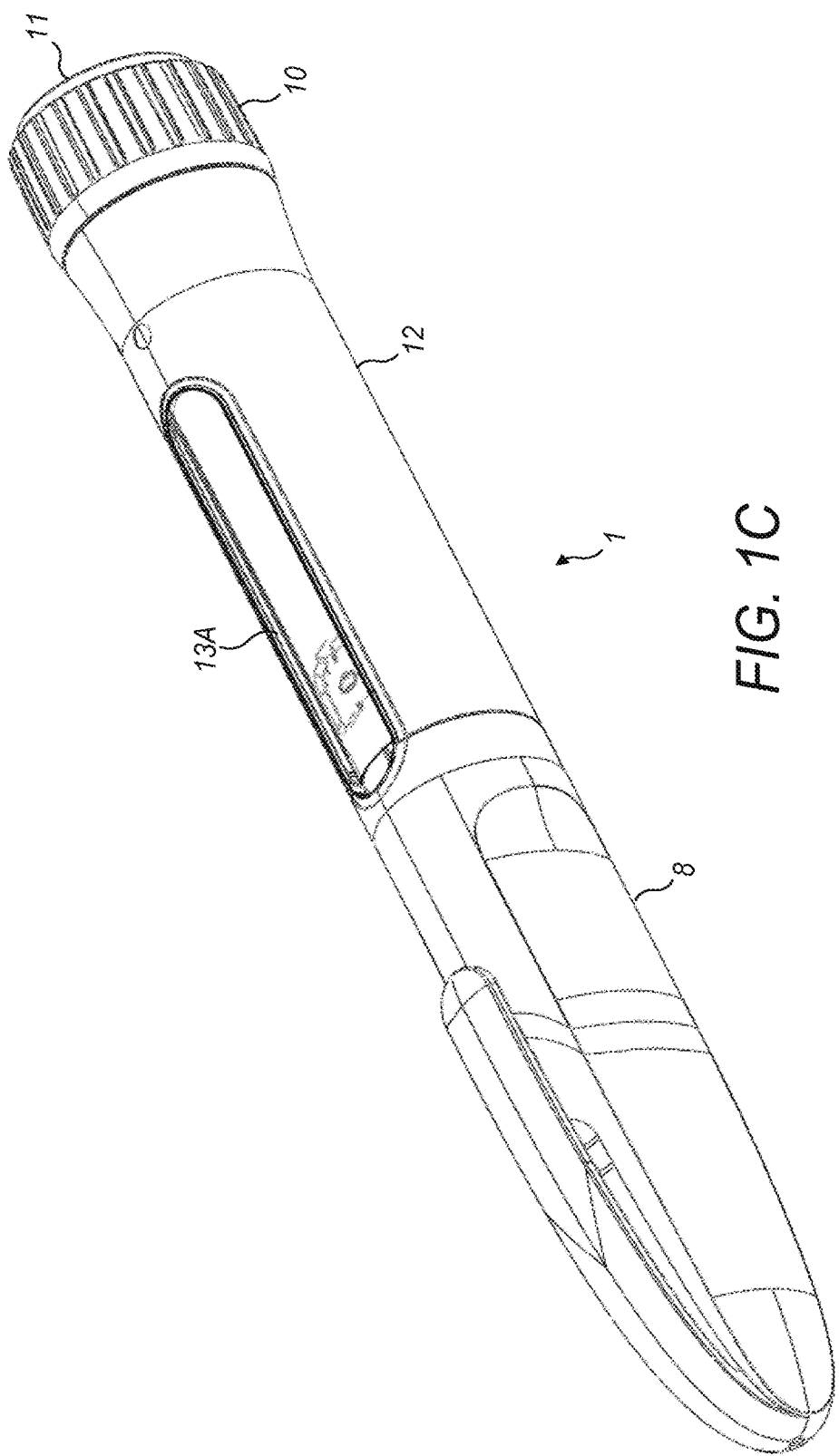
FIG. 1C is an isometric view of the drug delivery device with a cap in place.
Figure 1D:
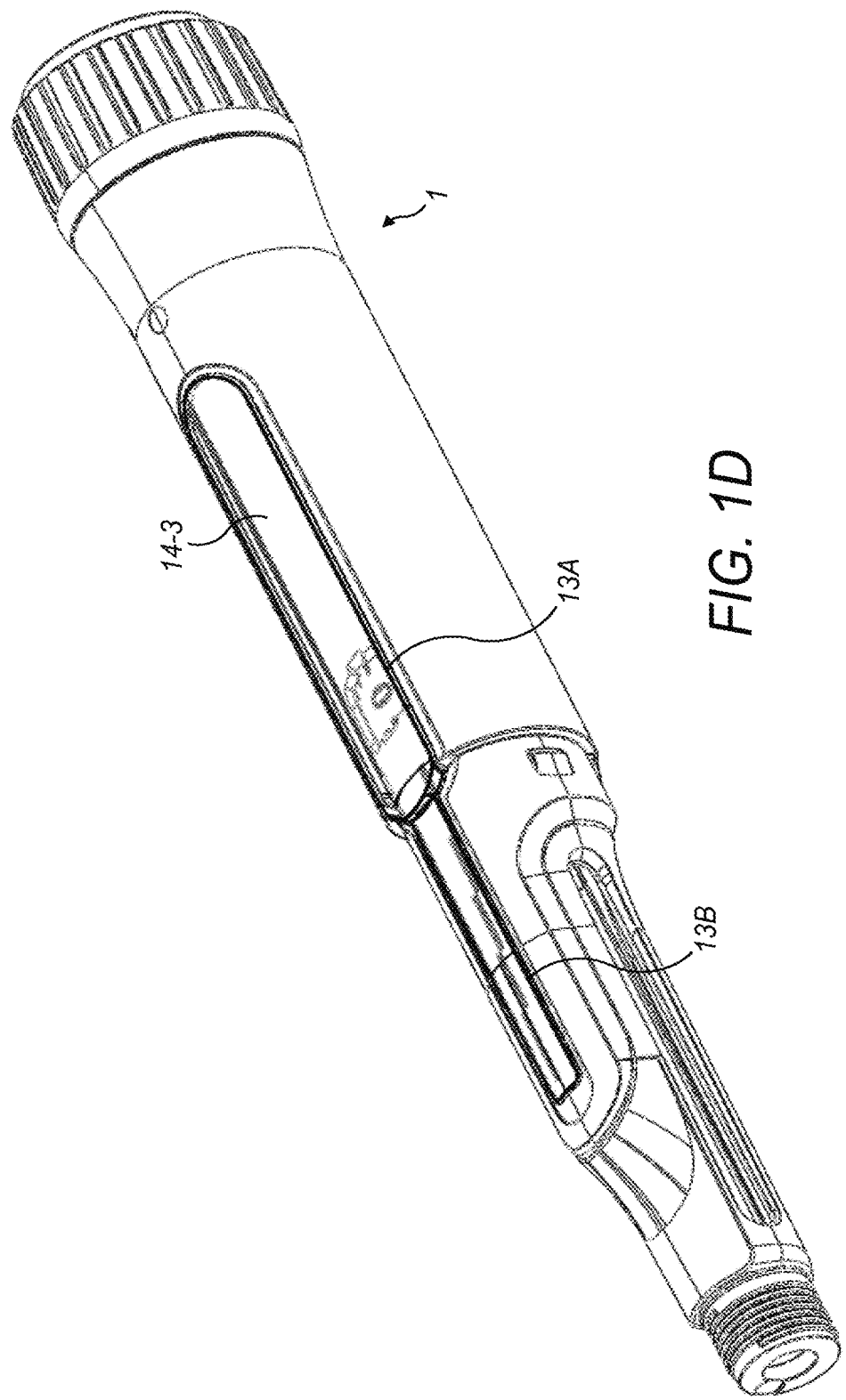
FIG. 1D is an isometric view of the drug delivery device with the cap removed.

In brief, the specification describes a drug delivery device, for instance an injection device, including a number sleeve having markings (e.g. a code) thereon. A dose setting or dialling mechanism of the device is configured to rotate the number sleeve without axially moving the number sleeve as a dose dialled is increased or decreased in a dose setting/dialling mode. The device includes a drive mechanism that causes expulsion of a dialled dose upon application of a driving force in a dose delivery mode. In addition to a first window, through which a user can read numbers indicating a currently set dose, a second window is provided. The second window is located at a fixed axial position on the main body and is coincident with the markings on the number sleeve.

An add-on device (or clip on device, or supplementary device) is a sensor device and includes an optical sensor that can view the markings through the second window and thus determine the rotational position of the number sleeve, to determine the dialled dose with a high resolution. The number of rotations of the number sleeve is determined through use of a separate sensor, to allow the dialled dose when this corresponds to more than one revolution of the number sleeve. The optical sensor that views the markings through the second window is used to detect whether a part of a drive mechanism, in particular, an end of a drive sleeve, is coincident with the window and thus is visible through the window. The presence, absence or location of the drive sleeve is used to determine whether the injection device is in dose setting mode or dose delivery mode. In the main embodiment, the drive sleeve is visible only when the injection device is in the dose delivery mode, so the detection of the absence of the drive sleeve through the second window is used to determine that the injection device is in dose setting mode and the detection of its presence is used to determine that the injection device is in dose delivery mode. The sensor device is operable to record and manage dose history information.

In the description and drawings, like reference numerals refer to like elements throughout.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml). In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

FIGS. 1A to 1D show views of a drug delivery device 1, in this example an injection device, with which a sensor device (also referred to as a supplementary device—not shown) according to various embodiments of the disclosure may be used.

The drug delivery device 1 of FIGS. 1A to 1D is configured such that a user is able to adjust the drug dosage (or number of drug doses) that is to be delivered (or dispensed) using the device 1. In the example of FIGS. 1A to 1D, this is achieved by rotating (or dialling) a dose selector 10 which causes an internal dialling mechanism (not shown) to adjust an amount of the drug that is to be dispensed once a drug delivery mechanism (not shown) is actuated. In this example, the drug delivery mechanism is actuated by pressing a button 11 on the proximal end of the device 1.

The drug delivery device 1 comprises an external housing 12 in which is formed at least one aperture or window 13A, 13B. As will be appreciated, an aperture may simply be a cut-away area of the external housing 12, whereas a window may be a transparent portion of the housing through which components of the device may be seen. For convenience, the at least one aperture or window 13A, 13B, will hereafter simply be referred to as the at least one window.

The at least one window 13A, 13B allows a movable gauge element 14 to be visible from the exterior of the housing 12. The drug delivery device is configured such that as the dose selector 10 is dialled, the movable gauge element 14 is caused to be moved thereby to indicate a selected dose to the user. More specifically, as the dose selector 10 is dialled, the gauge element 14 moves axially along an underlying surface 15A, 15B thereby to indicate the selected dose. In the example of FIGS. 1A to 1D, a surface 15A underlying at least part of the gauge element 14 comprises a number sleeve 15A. The number sleeve 15A has numbers indicative of drug doses provided on its outer surface, with the number indicating the currently selected dose being visible through the at least one window 13A, 13B. In this example, the number sleeve 15A is visible through a gauge window (or aperture) 14-1 formed in the movable gauge element. Other parts of the movable gauge element 14 are discussed below.

The view of the drug delivery device 1 shown in FIG. 1A illustrates the situation before any dialling has been performed. Consequently, the movable gauge element 14 is at its first (or initial) position at a first end of the path along which it is able to move. In this example, when the movable gauge element 14 is at the first end of its path, the portion of the number sleeve 15A that is visible through the gauge window 14-1 shows the number zero (i.e. a zero dose).

The view of the drug delivery device 1 shown in FIG. 1B illustrates the situation after dialling has been performed. Consequently, the movable gauge element 14 has moved axially along the path that is visible through the first window 13A away from its first position. In this example, the device 1 has been dialled to its maximum dose and as such, the movable gauge element 14 has moved to the second end of its path. The maximum dose in this example is "100" and so the portion of the number sleeve 15A that is visible through the gauge window 14-1 shows the number "100".

The delivery mechanism actuated by the button 11 may be injection. Injection is the process by which a bung or piston (not shown) is moved from a proximal location within a syringe (not shown) to a more distal location within the syringe in order to force a medicament from the syringe through a needle (not shown). In some embodiments, a drive spring (not shown) is under compression before the drug delivery device 1 is activated. A proximal end of the drive spring can be fixed within a proximal region of the housing 12, and a distal end of the drive spring can be configured to apply a compressive force to a proximal surface of the piston. Following activation, at least part of the energy stored in the drive spring can be applied to the proximal surface of the piston. This compressive force can act on the piston to move it in a distal direction. Such distal movement acts to compress the liquid medicament within the syringe, forcing it out of the needle.

In this example, the device 1 comprises first and second windows 13A, 13B (and a further window 63, as will be described below). The number sleeve 15A underlies and is visible through the first window 13A, whereas a further underlying element 15B underlies and is sometimes visible through the second window 13B. The further underlying element 15B may or may not include any numbers. The further underlying surface 15B is visually distinguishable from a second part 14-2 of the movable gauge element 14 which overlies it and which is configured to move axially along it. For instance, the second part 14-2 of the movable gauge element 14 may be of a different reflectance to the further underlying surface 15B. For example, one of the gauge element 14 and the underlying surface 15B may be of a light colour (e.g. may be made of a light coloured polymer) and the other may be of dark colour (e.g. may be made of a dark coloured polymer). The user may, therefore, be able to determine the selected dose by determining the proportion of the second window 13A in which the gauge element 14 (specifically, the second part 14-2) is visible compared to the proportion in which the further underlying surface 15B is visible. This can be seen from FIGS. 1A to 1D, in which, when the device 1 is dialled to its zero dose, the gauge element 14 covers the entire length of the path that is visible through the second window 13B. In contrast, when the device 1 is dialled to its maximum dose, none of the gauge element 14 is visible through the second window. Instead, the further underlying surface 15B is visible along the entire length of the path defined by the second window 13B.

The number sleeve 15A (which is also surface underlying the gauge element 14) is also visually distinguishable from the movable gauge element 14 which overlies it and which is configured to move axially along it. For instance, gauge element 14 may be of a different reflectance to the number sleeve 15A. For example, one of the gauge element 14 and the underlying surface 15A may be of a light colour (e.g. may be made of a light coloured polymer) and the other may be of dark colour (e.g. may be made of a dark coloured polymer). In the examples shown in the Figures, the number sleeve 15A and underlying surface 15B are of a higher reflectance than the movable gauge element 14.

FIGS. 2A to 2E are simplified schematics of components of a drug delivery device such as that of FIGS. 1A to 1D. The purpose of FIGS. 2A to 2E is to illustrate the operation of a drug delivery device 1 such as that of FIGS. 1A to 1D; they are not intended to be accurate representations of the exact design of the components.

Figure 2A:
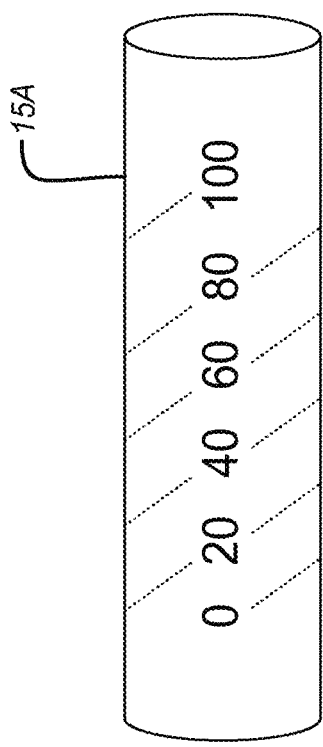

FIG. 2A is a simplified schematic of the number sleeve 15A. The sleeve 15A has numbers provided on its surface. In some examples, the numbers, ranging from the minimum dose to the maximum dose, may be provided helically around the surface of the number sleeve.

Figure 2B:
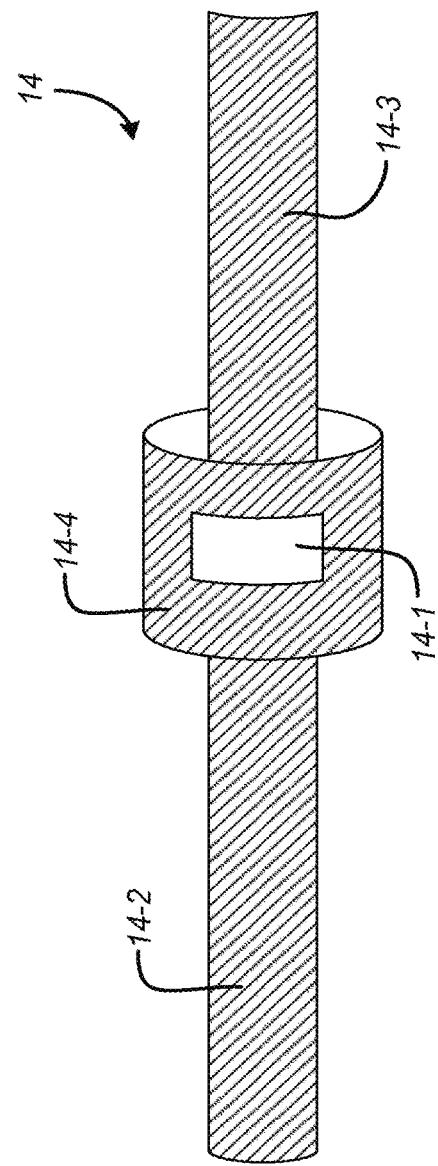

FIG. 2B is a simplified schematic of a movable gauge element 14. The gauge element 14 comprises a first section 14-4 in which the gauge window 14-1 is provided. In this example, the first section is 14-1 a collar which is configured to encircle the number sleeve 15A (as can be seen in FIGS. 2C and 2D). Extending in opposite directions from the first section 14-4 are the second part 14-2 and a third part 14-3. The second and third parts 14-2, 14-3 extend generally parallel to the longitudinal axis of the number sleeve.

The second part 14-2 of the movable gauge element is configured to extend from the first part 14-2 by a length sufficient to fill the entire second window 13B when the movable gauge is in its first position. The second part 14-2 may also serve to obscure a portion of the exterior surface of the number sleeve 15A, when the gauge element moves away from its first position. The third part of the movable gauge element 15-3 is configured to obscure a portion of the exterior surface of the number sleeve 15A, when the gauge elements moves between its first and second positions. In this way, only the portion of the number sleeve that underlies the gauge window 14-1 is visible through the first window 13A of the device housing 12.

The number sleeve 15A is rotatable about its longitudinal axis within the device housing 12. As such, the number sleeve 15A may be referred to as a movable (or rotatable) element. Rotation of the number sleeve 15A is in some embodiments caused by rotation of the dose selector 10.

The rotational movement $NS_R$ of the number sleeve 15A and axial movement $G_E$ of the gauge element 14 are interdependent. Put another way, the dialling mechanism of the device 1 is configured such that when number sleeve 15A is caused to rotate, the gauge element 14 is caused to move or translate axially along its path. Moreover, the degree of rotation of the number sleeve 15A corresponds proportionally to the extent of axial movement of the gauge element 14.

Figure 2E:
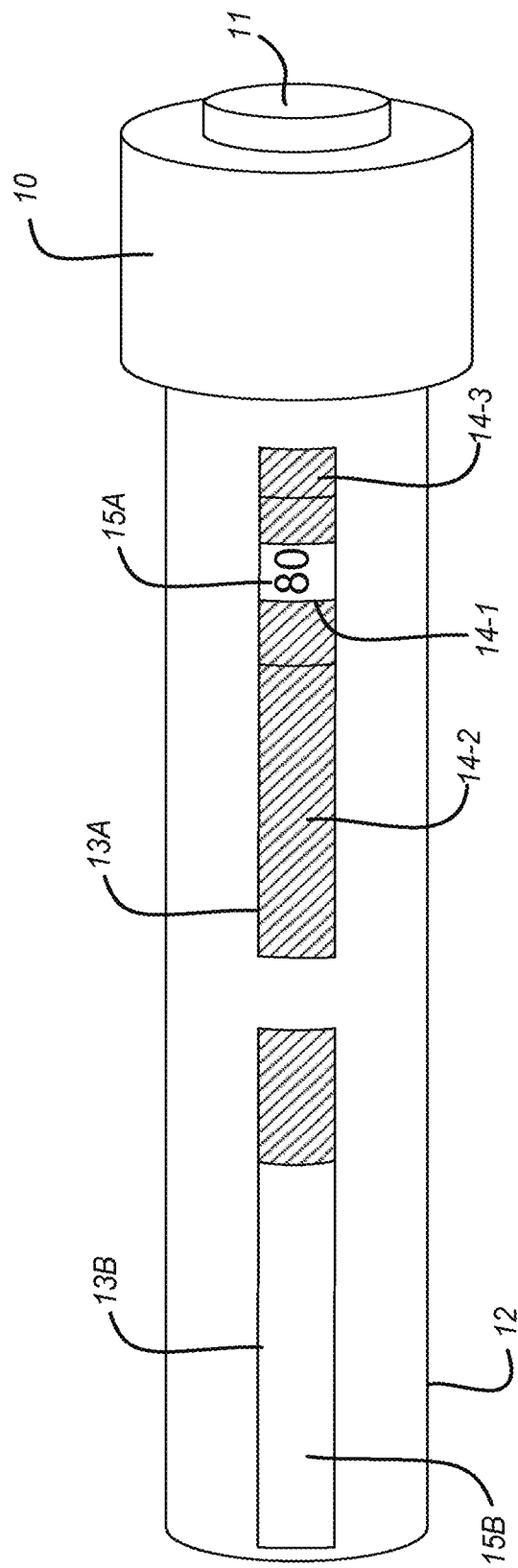

FIG. 2C shows the gauge element 14 in its initial position in which, in this example, it indicates a zero dose. FIG. 2D shows the number sleeve 15A and gauge element 14 following rotation of the number sleeve 15A and translation of the gauge element 14 from its first position. FIG. 2E shows this arrangement of FIG. 2D within a simplified version of the device housing 12.

Various dialling mechanisms for adjusting a dose to be delivered to a user which transform rotation of a dose selector 10 into rotational movement of a number sleeve 15 A and axial movement of a gauge element 14 (as described above) are known in the art. Two such mechanisms are described in WO2013/110538A1 and WO2008/145171A1. As such mechanisms (and also drug delivery mechanisms which cause delivery of the drug once the dose has been dialled) are known in the art, they will not be described herein in any detail.

Rotation of the dose selector 10 causes a corresponding rotation in the number sleeve 15A. The rotation of the number sleeve 15A is controlled by ratchet teeth (not shown) in a clutch plate (not shown), so that it can only stop in discrete detented rotational positions, corresponding to each drug unit.

According to embodiments, a sensor device includes one or more sensor arrangements configured to read information from the windows 13A and 13B, and a sensor arrangement configured to read information from a window at a different location on the device 1, as is described below.

Figure 3:
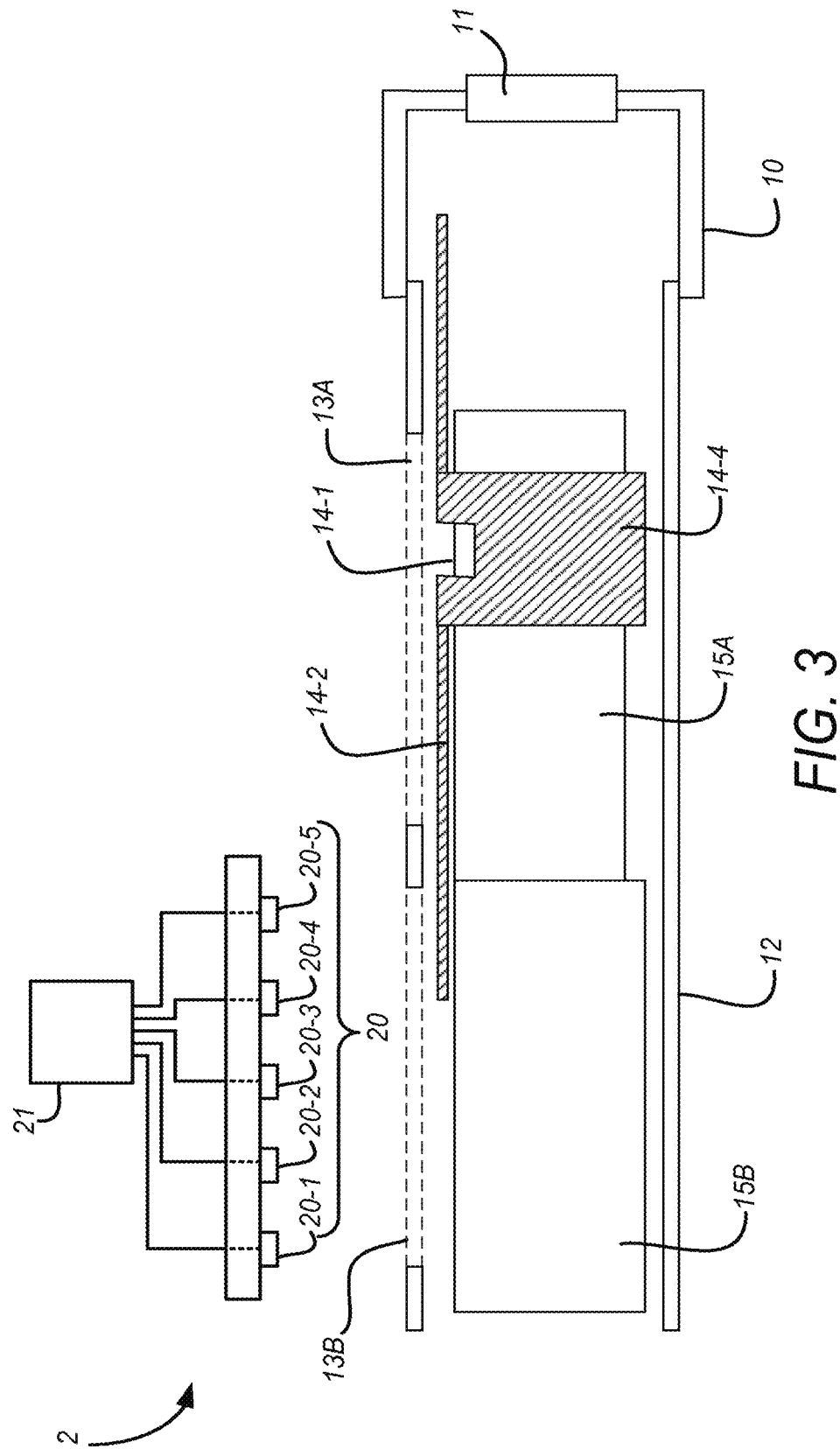
FIG. 3 shows is a simplified cut-away view of the drug delivery device components depicted in FIG. 2D in combination with part of a sensor device according to various embodiments of the disclosure.

FIG. 3 shows an extremely simplified cut-away view of the components of the delivery device 1 as depicted in FIG. 2D and a simplified schematic illustration of a sensor device 2 for use with a delivery device 1 such as that described with reference to FIGS. 1 to 2D.

The sensor device 2 is configured to determine a number of complete rotations of the number sleeve 15A from an initial position to the current position, which provides one component of the set or dialled dose (the other component is the amount of rotation within a complete rotation). One mechanism for making the determination will now be described with reference to FIGS. 3 and 4A to 4D, and another mechanism is described below with reference to FIG. 12.

Referring to FIG. 3, the sensor device 2 comprises an array 20 of optical sensors 20-1 to 20-5 arranged such that, when the sensor device 2 is in place on the drug delivery device 1, each optical sensor 20-1 to 20-5 in the array 20 is operable to detect light received from a different location along an externally visible path defined by one of the at least one window 13A, 13B. Each optical sensor 20-1 to 20-5 then outputs a signal indicative of an amount of detected light. The sensor device 2 further comprises circuitry 21 configured to receive the signals output from the optical sensors 20-1 to 20-5 of the array 20 and, based on the received signals, to determine information associated with a location along the path defined by the window 13A, 13B of the movable gauge element 14. The circuitry 21 may be further configured to control operation of the array 20.

When the sensor device 2 is in place adjacent an externally visible path of the drug delivery device 1, the optical sensors 20-1 to 20-5 of the array 20 are spaced along the path. The optical sensors 20-1 to 20-5 may be substantially equidistantly spaced from one another along a length generally corresponding to the length of the visible path. The length over which the optical sensors 20-1 to 20-5 are spaced may not be exactly the same as the length of the visible path along which the gauge element 14 moves but may be dependent on the length of the visible path with which the sensor device 2 is designed to be used.

In some embodiments, the array 20 of optical sensors 20-1 to 20-5 extends generally along an axis which, when the sensor device 2 is coupled to the delivery device 2, is generally parallel with the axis along which the moveable gauge element 14 is configured to move. The axis along which the array 20 of optical sensors extends is therefore also generally parallel with the longitudinal axis of the window 13A, 13B that it overlies. The axis along which the array 20 extends is also generally parallel to the longitudinal axis of the drug delivery device 1. The optical sensors 20-1 to 20-5 may be equidistantly spaced from one another along the axis.

Each of the optical sensors 20-1 to 20-5 has a corresponding light source (not shown) arranged to emit light towards the externally visible path (defined by the window 13A, 13B) when the sensor device 2 is attached to the drug delivery device 1. The light emitted by each light source is then reflected off the visible path back to the corresponding optical sensor 20-1 to 20-5. Each optical sensor 20-1 to 20-5 may be provided in a single package with its corresponding light source. Each of the optical sensors 20-1 to 20-5 may comprise a PIN photodiode, for example. Each of the light sources may, for instance, comprise an LED.

Because the visible path towards which the array 20 is oriented is formed by the gauge element 14 and/or the underlying element 15A, 15B, which are visually distinguishable from one another (e.g. because they are different colours), the amount of light reflected back to each of the optical sensors 20-1 to 20-5 will vary in dependence on the position of the movable gauge element 14 along its path.

The optical sensors of the array 20 may be configured such that, when the amount of detected light is one-side of a threshold, an output signal having a first value is provided to the circuitry 21 and, when the amount of detected light is on the other side of the threshold, an output signal having a second value is provided to the circuitry. In examples in which the optical sensors 20 are PIN photodiodes, when the amount of detected light is below a threshold, the output signal is LOW and when the detected light is above the threshold, the output is HIGH. As will be appreciated the exact threshold of the optical sensors and the values of the signals output by the sensors may be dependent on a number of factors including, for example, the bias applied to the sensors.

The drug delivery device 1 may be configured such that either one of the underlying surface 15A, 15B and the movable gauge element 14 has a reflectance which is sufficiently low such that the light reflected therefrom falls on one side of the sensor threshold. The other one of the underlying surface 15A, 15B and the movable gauge element 14 has a reflectance which is sufficiently high such that the light reflected therefrom falls on the other side of the threshold. In the examples described herein, the underlying surface 15A, 15B has a sufficiently high reflectance to overcome the sensor threshold, whereas the movable gauge element 14 has a sufficiently low reflectance so as not to surpass the sensor threshold. Consequently, in examples in which the sensors 20-1 to 20-5 are PIN photodiodes, sensors located above a section of path at which the gauge element 14 is externally visible output a LOW signal, whereas sensors located above a section of path at which the underlying element 15A, 15B is visible output a HIGH signal.

FIGS. 4A to 4D illustrate the operation of the sensor device 2 when the movable element is at different positions along its path. In this example, the array 20 comprises first to fifth optical sensors 20-1 to 20-5, with the first sensor 20-1 being located above a first end of the window 13B at which the movable gauge element 14 is present only when the minimum dose is dialled. The fifth sensor 20-5 is located above a second end of the window 13B at which the gauge element 14 is visible/present unless the maximum dose is dialled.

In FIG. 4A, the movable gauge element 14 is at its initial position (e.g. when the dose is at its minimum). Consequently, the dark coloured (and low reflectance) gauge element 14 covers the entire path underlying the array 20. As such, a sufficient quantity of light to surpass the threshold is not detected by any of the sensors 20-1 to 20-5. As such, all five sensors 20-1 to 20-5 output a LOW signal.

In FIG. 4B, the gauge element 14 has moved to approximately the 20% dose position. In this situation, the light coloured (and high reflectance) underlying surface 15B is visible to the first sensor 20-1. Consequently, sufficient light to surpass the threshold is reflected back from the underlying surface 15B to the first sensor 20-1 and so the first sensor outputs a HIGH signal. As the gauge element 14, is below each of the other sensors 20-2 to 20-5, these output a LOW signal.

In FIG. 4C, the gauge element 14 has moved to approximately the 40% dose position and so the light coloured (and high reflectance) underlying surface 15B is visible to the first and second sensors 20-1, 20-2, which therefore output a HIGH signal. The third to fifth sensors 20-3 to 20-5 output a LOW signal.

Finally, in FIG. 4D, the gauge element 14 has moved to approximately the 80% dose position and so the light coloured (and high reflectance) underlying surface 15B is visible to the first to fourth sensors 20-1 to 20-4, which output a HIGH signal. The fifth sensor element outputs a LOW signal.

From the above, it is clear how the signals output from the optical sensors 20-1 to 20-1 can be used by the circuitry 21 to determine the dialled dose. This is illustrated in Table 1 below:

TABLE 1

| Determined Dose | $1^{st}$ sensor output | $2^{nd}$ sensor output | $3^{rd}$ sensor output | $4^{th}$ sensor output | $5^{th}$ sensor output |
| --- | --- | --- | --- | --- | --- |
| 0% | LOW | LOW | LOW | LOW | LOW |
| 20% approx. | HIGH | LOW | LOW | LOW | LOW |
| 40% approx. | HIGH | HIGH | LOW | LOW | LOW |
| 60% approx. | HIGH | HIGH | HIGH | LOW | LOW |
| 80% approx. | HIGH | HIGH | HIGH | HIGH | LOW |
| 100% | HIGH | HIGH | HIGH | HIGH | HIGH |

Although the above example describes optical sensors having a threshold and two distinct outputs (HIGH and LOW), it will be appreciated that sensors which do not have such a threshold and which instead output a signal from which the amount of detected light is derivable (e.g. because the output signal is proportional to the amount of light detected) may instead be used. In such examples, the circuitry 21 is still configured to determine, based on the received signals, whether the movable gauge element 14 or the underlying surface 15A, 15B is visible to a particular optical sensor.

As will be appreciated, the array 20 of optical sensors 20-1 to 20-5 provides information from which the number of rotations of the number sleeve 15A, from the initial position, can be determined. The arrangement for determining the rotational position of the number sleeve 15A within a full rotation will now be discussed with reference to FIGS. 5 and 6A to 6D.

Figure 5:
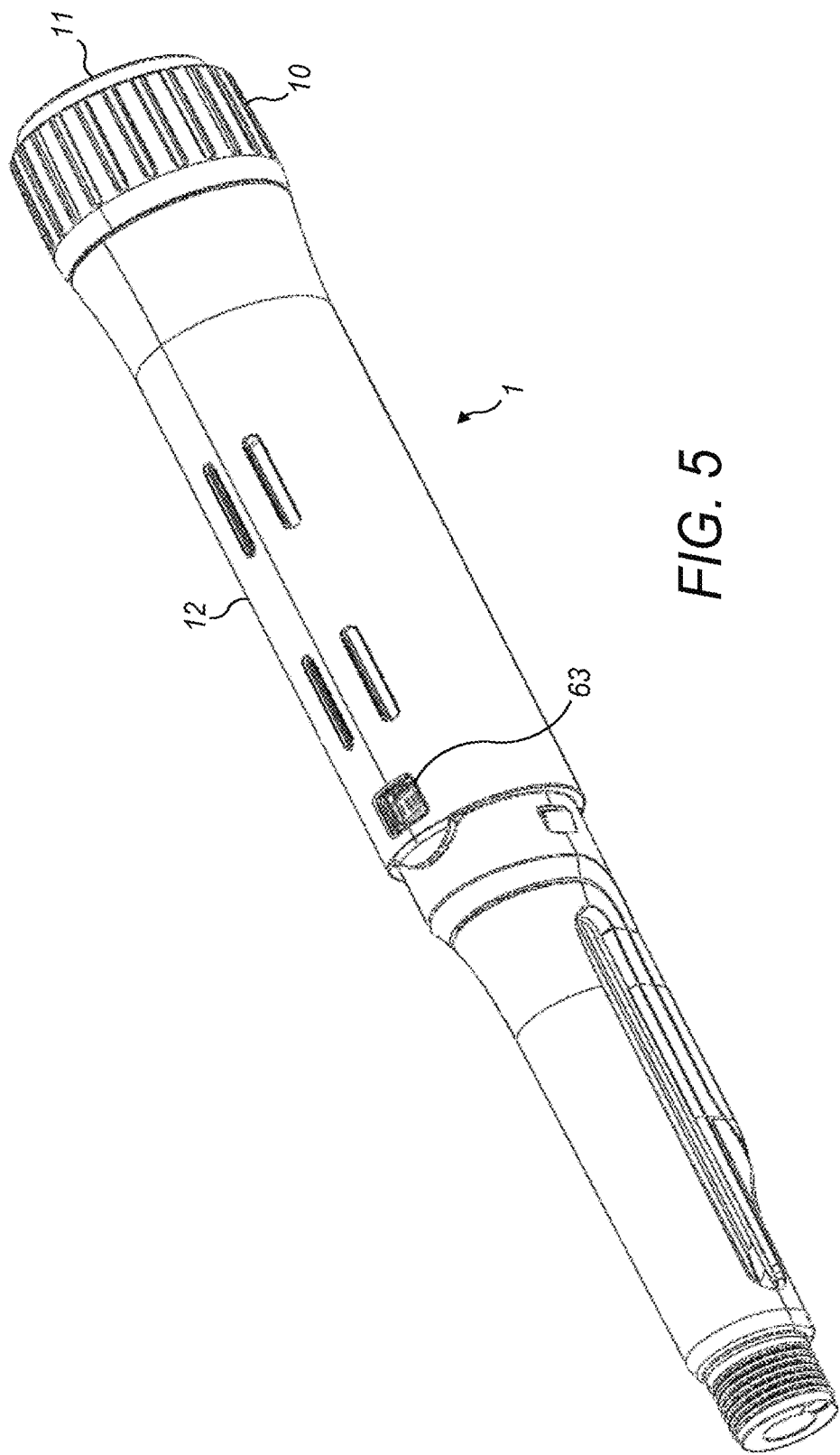
FIG. 5 shows an isometric view of the drug delivery device with a rear window visible.
Figure 7A:
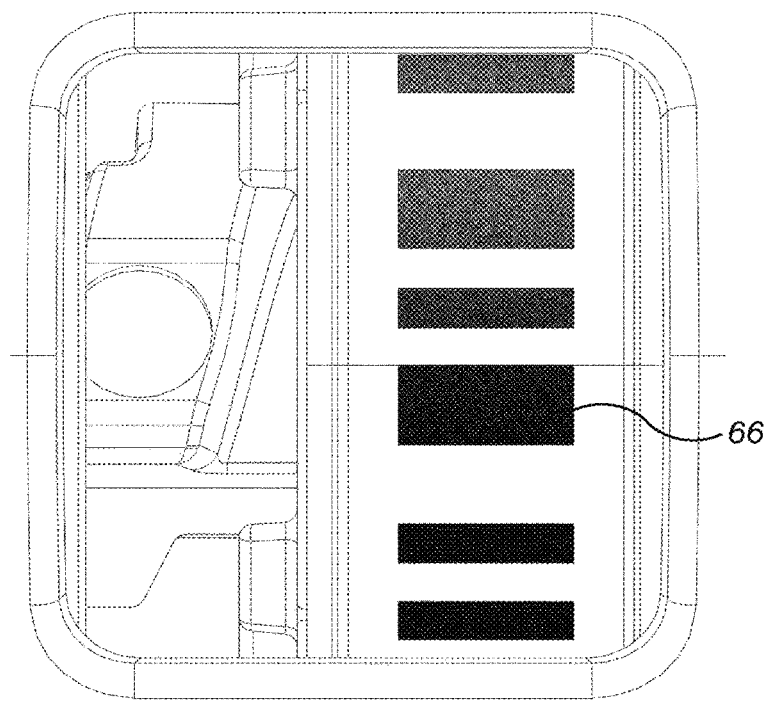
FIGS. 7A and 7B are views of the rear window of the drug delivery device in dose setting mode and dose delivery mode respectively.
Figure 7B:
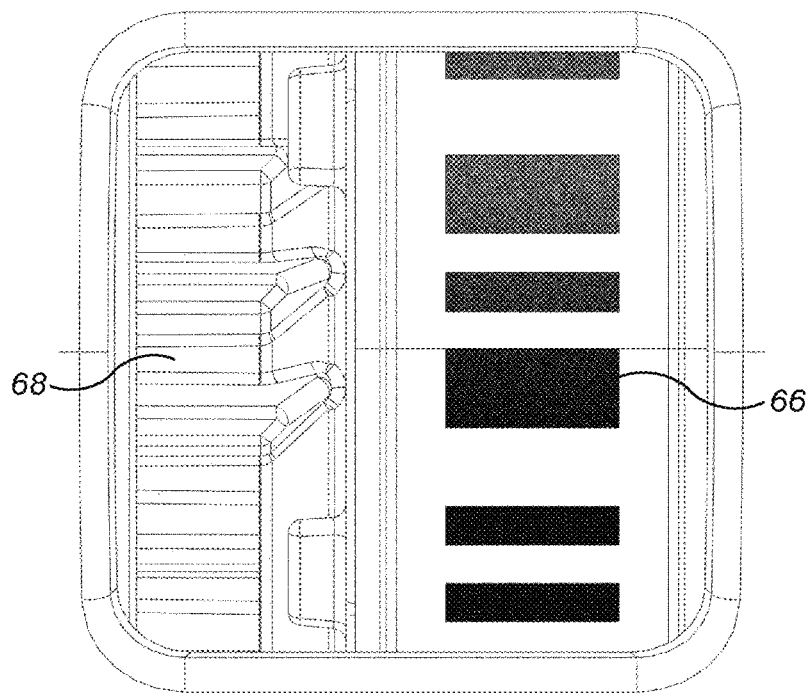

FIG. 5 shows that the drug delivery device 2 includes a further window or aperture 63 formed in the housing 12. The further window 63 is at a different location to the first and second windows 13A and 13B. In this example, the further window is located on the back of the device 1, at the 180 degree position relative to the first and second windows 13A and 13B. The further window 63 is located approximately half way along the housing 12. In particular, the location of the further window 63 coincides with the end of the number sleeve 65A such that the number sleeve 65A is visible through the further window 63. Also, part of the interior of the device 1 that is distally located compared to the end of the number sleeve is visible through the further window 63. This is most clearly seen from FIGS. 7A and 7B.

Figure 6A:
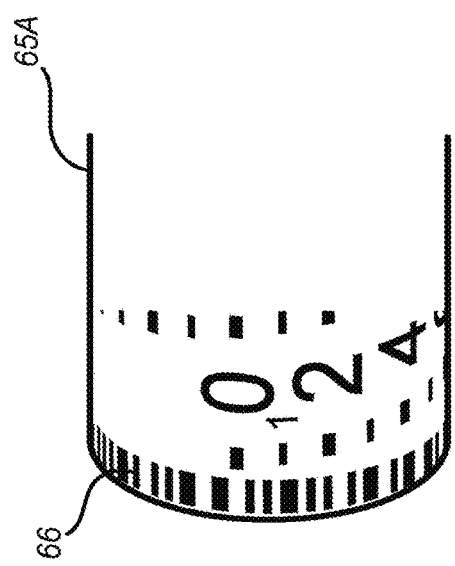
FIGS. 6A to 6C are illustrative simplified views of various components of the drug delivery device with which sensor devices according to various embodiments of the disclosure may be used.
Figure 6B:
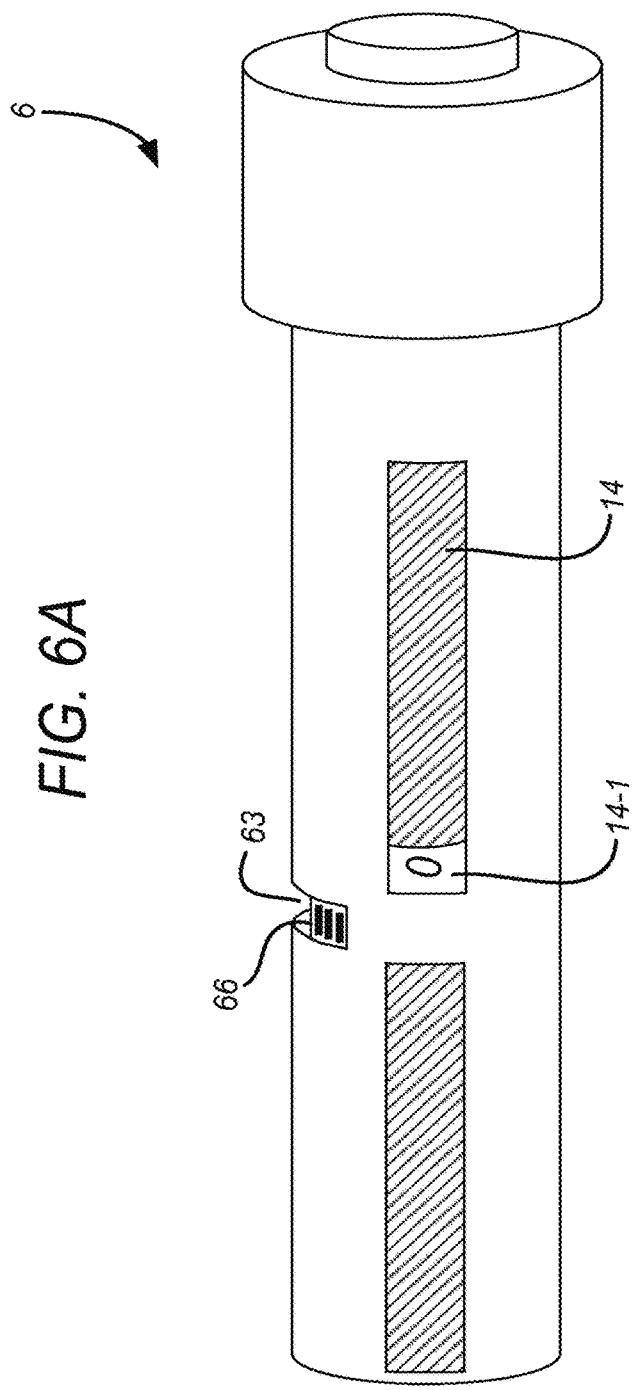
Figure 6C:
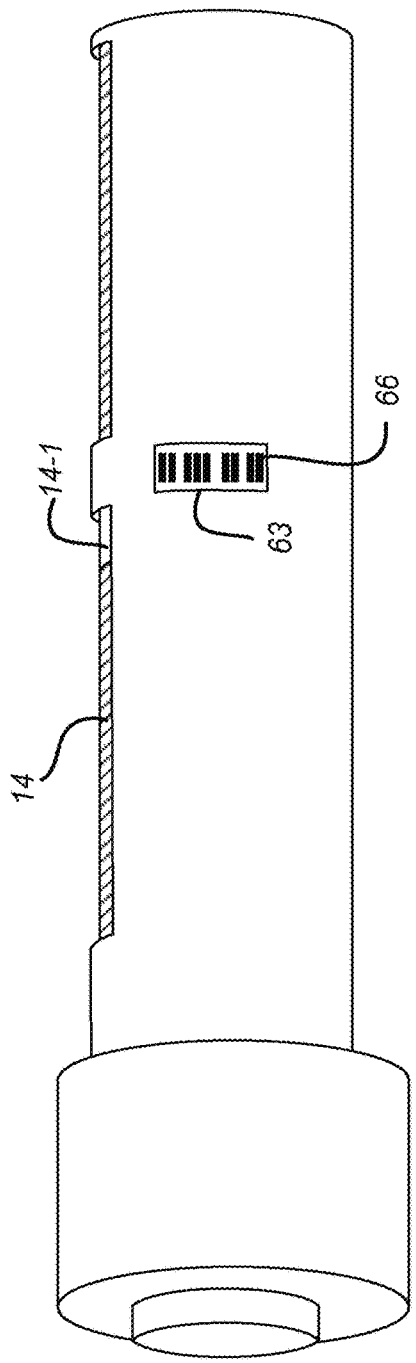

FIG. 6A shows an example of a rotatable element 65A, in this instance a number sleeve 65A, which may form part of a drug delivery device 1 for use with sensor devices 2 according to embodiments of the disclosure. FIGS. 6B and 6C show two different simplified views of a delivery device 1 including the rotatable element 65A of FIG. 6A. The delivery device of FIGS. 6A and 6B may be generally the same as that described with reference to the previous Figures except for the differences described below. The number sleeve 15A of the above-described Figures corresponds with the rotatable element 65A of these Figures.

As with the previously described delivery device 1, the rotation of the rotatable element 65A is interdependent with the axial movement of the movable gauge element 14. The degree of rotation may be proportional to the axial movement of the movable gauge element 14. The rotatable element 65A has, provided around its exterior surface, a visually-distinguishable code 66 for allowing its rotational orientation to be determined. For instance, the code may enable determination by the sensor device 2 as to whether the rotational orientation is zero degrees, 90 degrees, 180 degrees, 270 degrees. A rotation of zero degrees corresponds to the initial orientation of the rotatable element 65A when the dose of the delivery device 1 is dialled to its minimum. It also corresponds to the orientation after every complete rotation of the rotatable element 65A. In other examples, the code 66 may allow a higher or lower accuracy with regards the rotational orientation of the rotatable element 65A. For instance, the code 66 may allow an accuracy of 15, 30 or 45 degrees or may allow an accuracy of only 180 degrees. Advantageously, the code 66 allows an accuracy of 15 degrees. This corresponds to 24 doses per revolution of the rotatable element/number sleeve 65A. Because the number sleeve 65A detents into discrete positions, the rotational position is equivalent to a number of drug units, where the number is between zero and the number of drug units that correspond to a full rotation of the number sleeve 65A.

The code 66 may take any suitable form so long as it allows the rotational orientation of rotatable element to be determined by the sensor device 2. In this example, the code 66 is provided at an end of the number sleeve 65A. The code 66 may be printed in visible ink. Although only on row of code is shown, multiple rows may be provided. Multiple rows can allow more information to be provided.

The code 66 may be provided on a recessed portion of the number sleeve 65A. The recess protects the code 66 from abrasion when the number sleeve 65A rotates.

The housing 12 of the drug delivery device 1 includes the third aperture or window 63 through which a portion of the rotatable element 65A, on which part of the code 66 is provided, is visible.

The further window 63 is positioned and oriented relative to the rotatable element 65A such that a portion of the code is externally visible through the further window 63 regardless of the rotational orientation of the rotatable element 65A. The further window 63 is positioned and oriented relative to the rotatable element 65A such that, as the rotatable element rotates through a single complete rotation, a different section of the code 66 is visible at each rotational orientation. The further aperture is, in this example, provided on a different side of the device housing 12 (or, if the housing is cylindrical or otherwise rounded, around the exterior surface of the device housing 12) from the at least one window 13A, 13B through which the movable gauge element 14 is visible. In this way, the movable gauge element 14 does not obstruct the code from view.

Figure 6D:
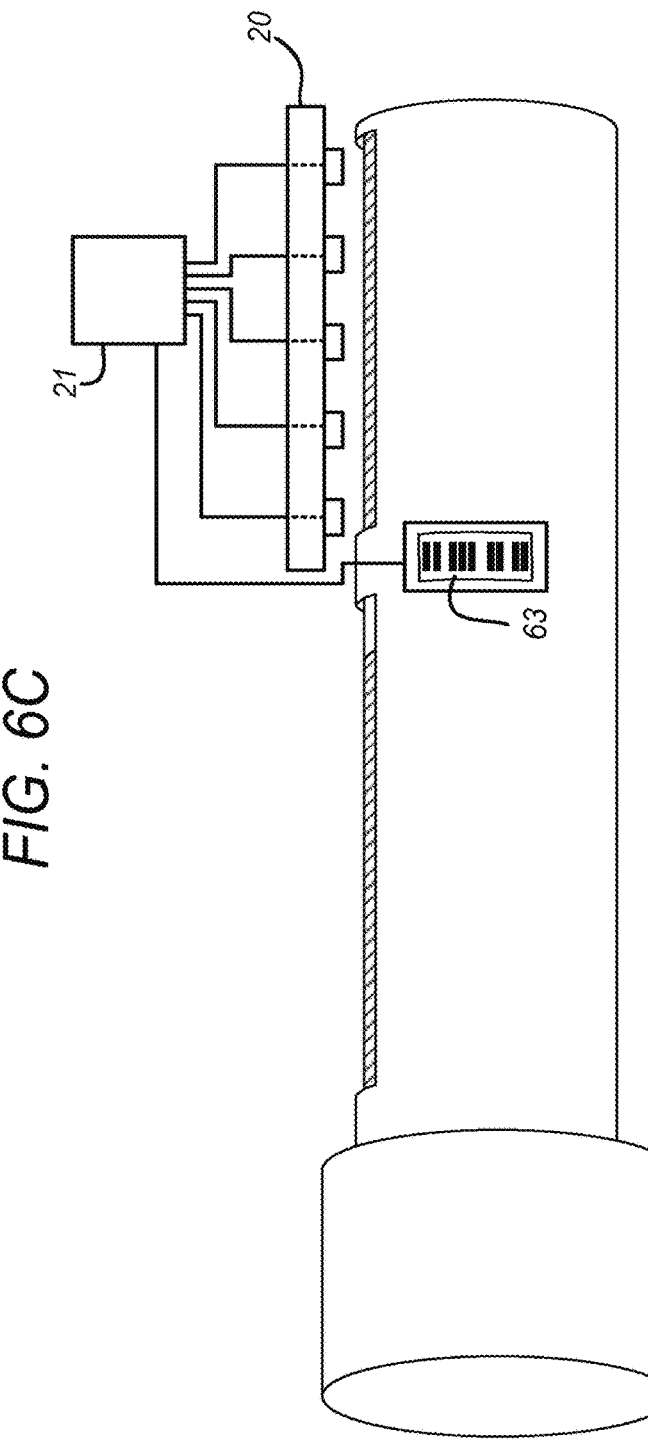
FIG. 6D is a simplified view of a sensor device according to embodiments of the disclosure in combination with the drug delivery device of FIGS. 6A to 6C.

As shown schematically in FIG. 6D, the sensor device 2 may, in addition to the array 20 of optical sensors 20-1 to 20-5, include a further sensing arrangement 23. The sensing arrangement 23 is arranged within the sensor device 2 such that, when the sensor device 2 is attached to the drug delivery device 1, the sensing arrangement 23 is operable to read the code 66 that is externally visible on the drug delivery device through the further window 63. The further sensing arrangement 23 may be a camera and may include a camera sensor and a lens arrangement.

The sensing arrangement 23 may be of any suitable type as long as it enables the code 66 to be read. For instance, the sensing arrangement may be an optical sensing arrangement comprising a camera or a small array of sensing elements, a magnetic or inductive sensing arrangement or a conductance/resistance sensing arrangement. Advantageously, the sensing arrangement is an optical sensing arrangement.

The circuitry 21 of the sensor device 2 of FIG. 6D is configured to determine, based on the code 66, a current dose to which the device 1 is dialled, based on the code 66 and the signals output from the optical sensors of the array 20. For instance, the signals output from the array 20 may be utilised by the circuitry 21 to determine the number of complete rotations of the rotatable element 65A that have occurred and the code 66 read by the sensing arrangement 23 may be utilised to determine the rotational orientation of the rotatable element 65A. Put another way, the signals output from the array 20 may be used to determine roughly the extent of axial translation of the moveable gauge element, with the code 66 read by the sensing arrangement being used with the rough determination to more precisely determine the extent of translation of the movable gauge element 14 (thereby to determine the currently dialled dose).

The array 20 may comprise the same number of optical sensors 20-1 to 20-5 as the number of complete rotations of the rotatable element 65A that are required to move the movable gauge element 14 from its initial to final position. The sensors 20-1 to 20-5 may be distributed adjacent the visible path of the movable gauge element such that after every complete rotation of the rotatable element 65A, the output of a successive optical sensor in the array 20 changes. For instance, using the example described with reference to FIGS. 4A to 4D and Table 1, after the first complete rotation of the rotatable element 65A, the output of the first sensor 20-1 in the array 20 changes from LOW to HIGH. After the second rotation, the output of the second sensor 20-2 changes from LOW to HIGH. After the third complete rotation, the output of the third sensor 20-2 changes from LOW to HIGH and so on until the fifth complete rotation at which point the output of the fifth sensor 20-5 changes from LOW to HIGH. It will thus be appreciated that the signals output by the sensors of the array 20 can be used to determine the number of complete rotations.

The code 66 read by the sensing arrangement 23 is then used by the circuitry 21 to determine the extent of any partial rotations of the rotatable element 65A. The determined extent of partial rotation of the rotatable element 65A is then combined with the determined number of complete rotations to determine the currently dialled dose of the drug delivery device 1. This determination is illustrated in Table 3 below:

TABLE 3

| Dose | $1^{st}$ sensor output | $2^{nd}$ sensor output | $3^{rd}$ sensor output | $4^{th}$ sensor output | $5^{th}$ sensor output | Partial Rotation (degrees) |
|---|---|---|---|---|---|---|
| 0% | LOW | LOW | LOW | LOW | LOW | 0 |
| 10% | LOW | LOW | LOW | LOW | LOW | 180 |
| 20% | HIGH | LOW | LOW | LOW | LOW | 0 |
| 30% | HIGH | LOW | LOW | LOW | LOW | 180 |
| 40% | HIGH | HIGH | LOW | LOW | LOW | 0 |
| 50% | HIGH | HIGH | LOW | LOW | LOW | 180 |
| 60% | HIGH | HIGH | HIGH | LOW | LOW | 0 |
| 70% | HIGH | HIGH | HIGH | LOW | LOW | 180 |
| 80% | HIGH | HIGH | HIGH | HIGH | LOW | 0 |
| 90% | HIGH | HIGH | HIGH | HIGH | LOW | 180 |
| 100% | HIGH | HIGH | HIGH | HIGH | HIGH | 0 |

It will be understood that the accuracy of the sensor device 2 can be improved by increasing the accuracy with which partial rotations can be determined. For instance, in the above example, if quarter rotations (i.e. every 90 degrees) were instead identifiable, the circuitry 21 would be able to determine the dialled dose to an accuracy of 5%. In embodiments with greater resolution of rotational position, e.g. to 15 degrees, the circuitry is able to determine a dialled or set dose of between zero and 120 units, corresponding to five rotations and 24 doses per rotation.

The sensor device 2 is configured to process signals provided by the further sensing arrangement 23 (or a still further sensing arrangement—not shown) to determine from inspection of the drug delivery device 1 in the vicinity of the further window 63 whether the drug delivery device 1 is in a dose setting mode or a dose delivery mode. In particular, the sensor device 3 is configured to determine a location, presence or absence of a part of a drive mechanism that is viewable through the further window 63.

Figure 8A:
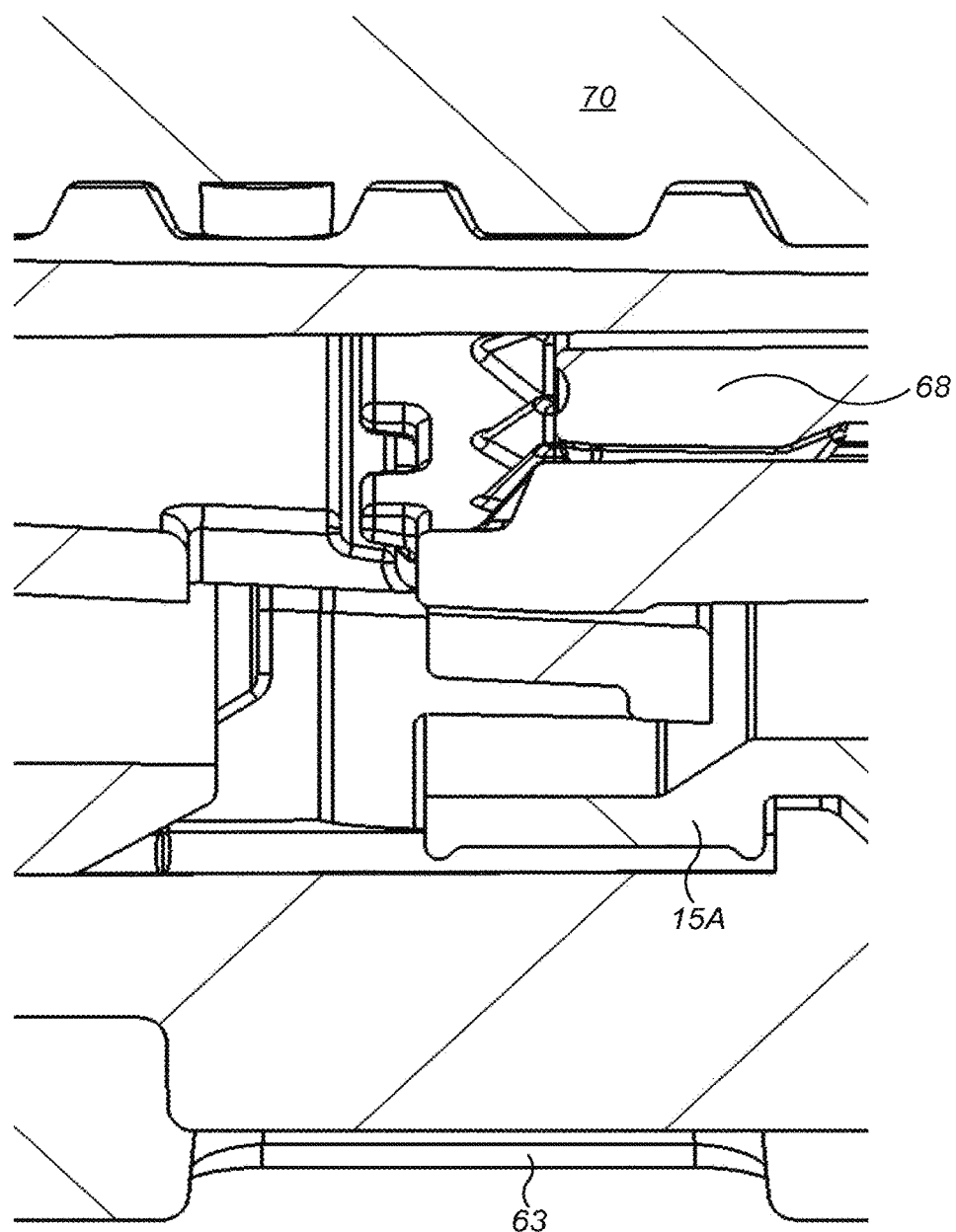
FIGS. 8A and 8B are longitudinal section views of the drug delivery device in the vicinity of the rear window in dose setting mode and dose delivery mode respectively.
Figure 8B:
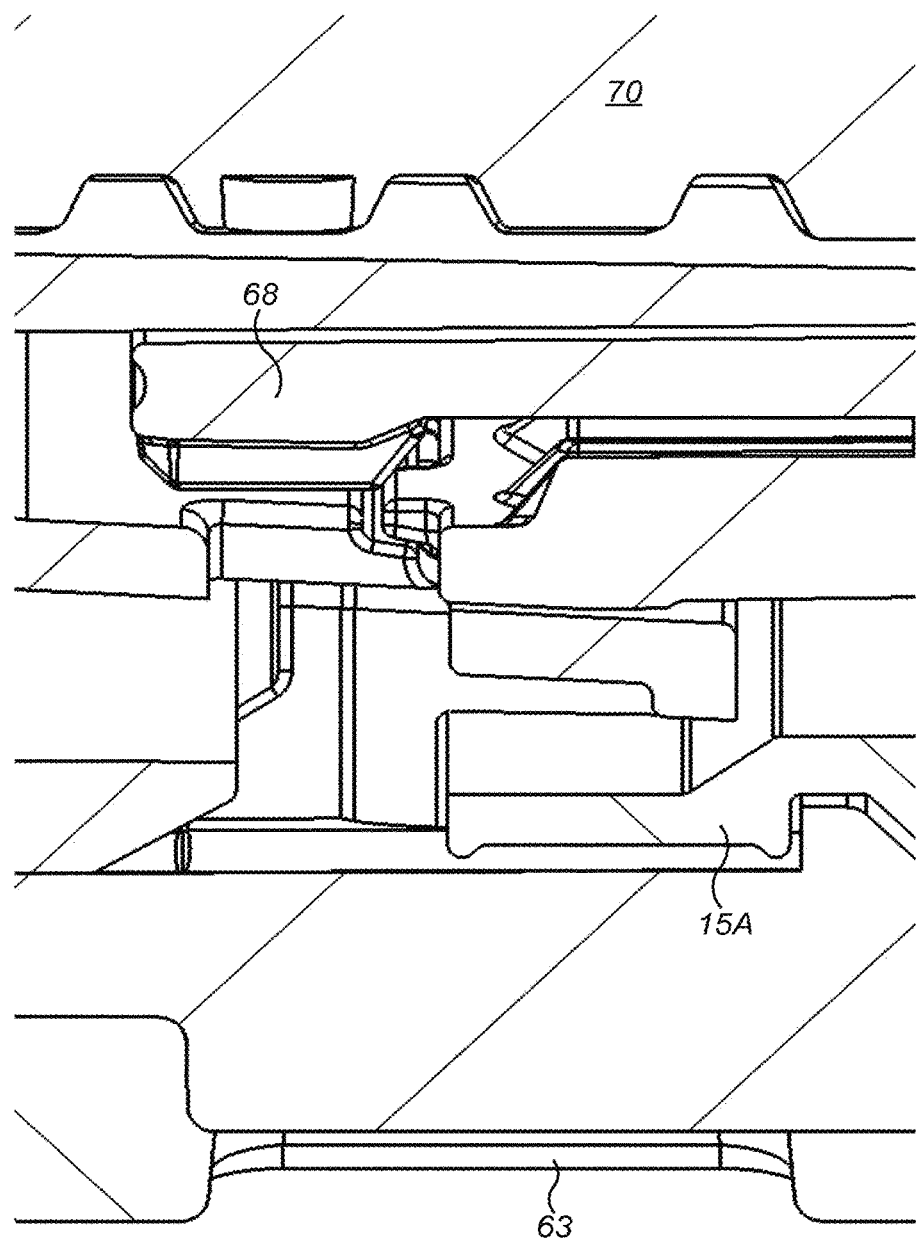

In particular, the further sensing arrangement 23 is arranged to have a field of view that encompasses all of or almost all of the area of the further window 63. As such, the further sensing arrangement 23 views the scene shown in FIG. 7A when the drug delivery device 1 is in the dose setting mode. The scene may be viewed by the sensing arrangement 23 from the side, rather than directly as shown in the Figures. As can be seen from FIGS. 7A and 8A, in the dose setting mode, the end of the number sleeve 15A, on which is provided the code 66, occupies about half of the area of the further window 63. The other half of the window permits observation of a drive screw 70, which is shown at the top of FIG. 8A. The further sensing arrangement 23 views the scene shown in FIG. 7B when the drug delivery device 1 is in the dose delivery mode. As can be seen from FIGS. 7B and 8B, in the dose delivery mode, the end of the number sleeve 15A, on which is provided the code 66, still occupies about half of the area of the further window 63. However, the other half of the window 63 permits observation of a drive sleeve 68, which now resides at a location in the radial direction between the drive screw 70 and the further window 63. Triggering of the button 11 causes the drive mechanism within the drug delivery device 1 to be activated. This results in movement of various components in a proximal direction, that is away from the button 11. The drive sleeve 68 is one component that is moved in a proximal direction. In particular, the drive sleeve 68 has moved from a position in which it was substantially surrounded by the number sleeve 15A, at least in the vicinity of the further window 63, to a position in which a proximal end of the drive sleeve 68 extends from the number sleeve 15A. In the extended position, the drive sleeve obstructs the view of the drive screw 70, which is shown at the top of FIG. 8B, from the further window 63. As such, when in the dose delivery mode, it is the number sleeve 15A and the drive sleeve 68, rather than the drive rod 70 or other internal components of the drug delivery device 1, that are viewable through the further window 63. The viewability of the drive sleeve 68 is facilitated by a cut-out in a clutch. The drive screw 70 is not moved axially, but is rotated during drug delivery.

The drive sleeve 68 is configured so as to facilitate fast and reliable detection of its presence or absence in the window 63. In particular, the drive sleeve 68 is provided with an appearance that contrasts in colour with surrounding parts, in particular the number sleeve 15A and any other parts that are visible through the further window 63. For instance, the drive sleeve may be dark colour, for instance black, dark grey or dark blue, and the number sleeve (apart from the code 66) and the other visible components may be a light colour, such as white or yellow. The other visible components may instead be substantially transparent. The internal components that are viewed through the window when the drive sleeve 68 is not present are a similar colour to the number sleeve 15A are a similar colour to and any components that are visible in both of the dose selecting and dose delivery modes. The contrast may be in the non-visible spectrum, for instance ultra-violet or infra-red. Contrast may be provided by providing different luminescence or reflectivity to different components. Different colours may be provided by material selection or by coating, such as printing, of either or both components 68, 15A.

The circuitry 21 is configured to process signals provided by the further sensing arrangement 23 to determine the presence, absence or location of the drive sleeve 68 in the further window 63. From this, the circuitry 21 determines that the drug delivery device is in the dose setting mode (if the drive sleeve 68 is absent) or is in the dose delivery mode (if the drive sleeve 68 is present). If the circuitry 21 determines that the drive sleeve 68 is partly present, the circuitry 21 may determine that the drug delivery device is transitioning between the dose delivery mode and the dose setting mode.

By providing the drive sleeve 68 in a colour that contrasts with the number sleeve 15A and other viewable components, the presence or absence of the drive sleeve 68 in the further window 63 can readily be determined by processing of the signals from the further sensing arrangement 23.

Using knowledge of the mode of operation of the drug delivery device 1 and the set dose at different times, the circuitry 21 can determine the delivered dose. In a drug delivery device in which all of the set dose is delivered when the drive mechanism is activated, the dose is calculated as the set dose that was present at the time that the drug delivery device transitioned from the dose setting mode to the dose delivery mode. In a drug delivery device in which it is possible to deliver some (but not all) of a set dose, the dose is calculated as the set dose that was present at the time that the drug delivery device transitioned from the dose setting mode to the dose delivery mode minus the set dose that was present at the time that the drug delivery device subsequently transitioned from the dose delivery mode back to the dose setting mode.

Figure 9:
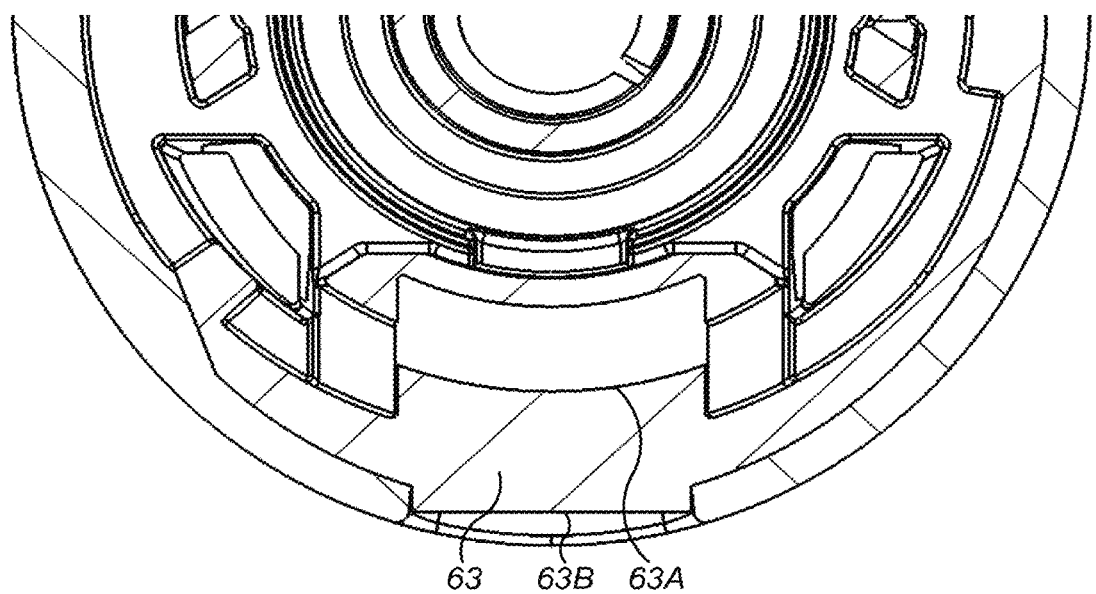
FIG. 9 is a sectional view across the drug delivery device in the vicinity of the rear window.

FIG. 9 shows the profile of the further window 63. An internal surface 63A of the further window 63 has a first profile. An external surface 63B of the further window 63 has a different profile.

The profiles of the surfaces 63A and 63B may be chosen to provide magnification, i.e. to provide the further window 63 with an optical power. This can improve effectiveness of the further sensing arrangement 23 and the circuitry 21 in determining the mode of operation of the drug delivery device 1 and the rotational position of the number sleeve 15A.

The profiles of the surfaces 63A and 63B may be chosen in addition or alternatively to divert the field of view of the sensing arrangement 23, in particular in a longitudinal direction relative to the housing 12, a lateral direction, or both.

The profiles of the surfaces 63A and 63B may be chosen in addition or alternatively to support parts internal to the drug delivery device 1.

The profile of the internal surface 63A is rounded and further advantageously is circular, which provides better mechanical support for the number sleeve 15A.

The profile of the external surface 63B is flat, and is recessed from the outside of the housing 12. This provides protection of the external surface 63B from abrasion.

Alternatively or additionally, the edges of the window 63 may be angled or roughened. This can allow illumination of the code 66 without reflecting light from an illuminating light source (not shown) to the further sensing arrangement 23.

Figure 10:
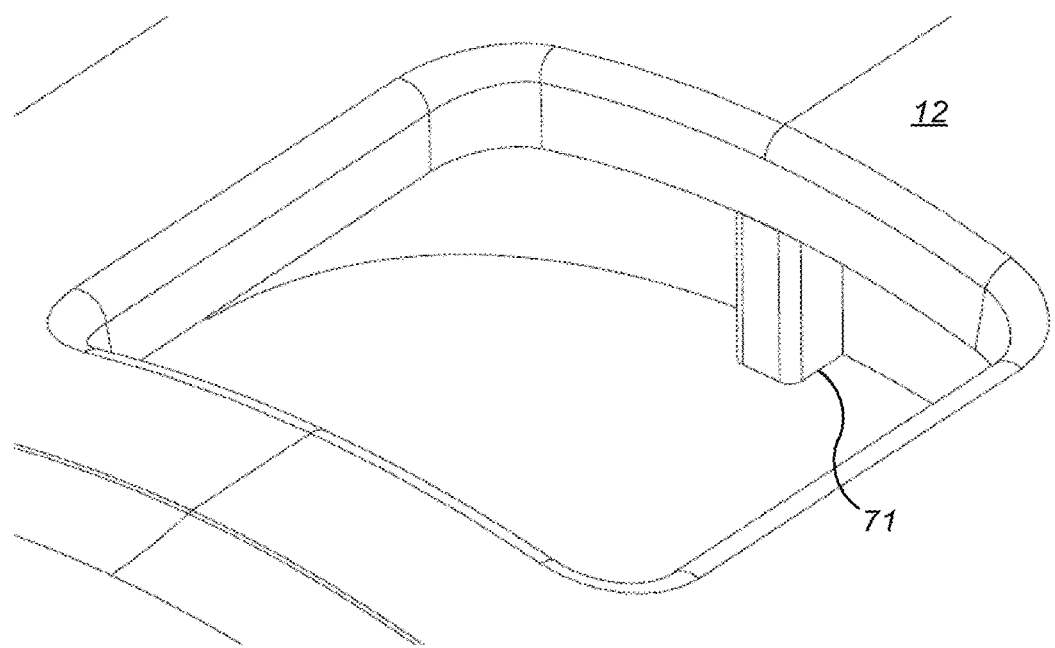
FIG. 10 is an isometric view of the rear window.

Because of geometric tolerances and free play between parts, the location of the code 66 relative to the further sensing arrangement 23 may vary between different devices produced by a manufacturing process. Where there is variation, it may be difficult to determine a difference between an image sensed by the sensing arrangement 23 for n units of drug on one device and an image for n+1 units of drug on another device. This problem is ameliorated by the use of a reference mark 71, as is shown in FIG. 10. The reference mark 71 is located at the edge of the further window 63. The reference mark 71 may be a protrusion which extends from the housing 12. The reference mark 71 may be hidden from view in that it is not visible when the drug delivery device 1 is viewed side on. However, the reference mark 71 is visible to the sensing arrangement 23, which views the scene in the further window 63 from the side of the window 63.

Figure 12:
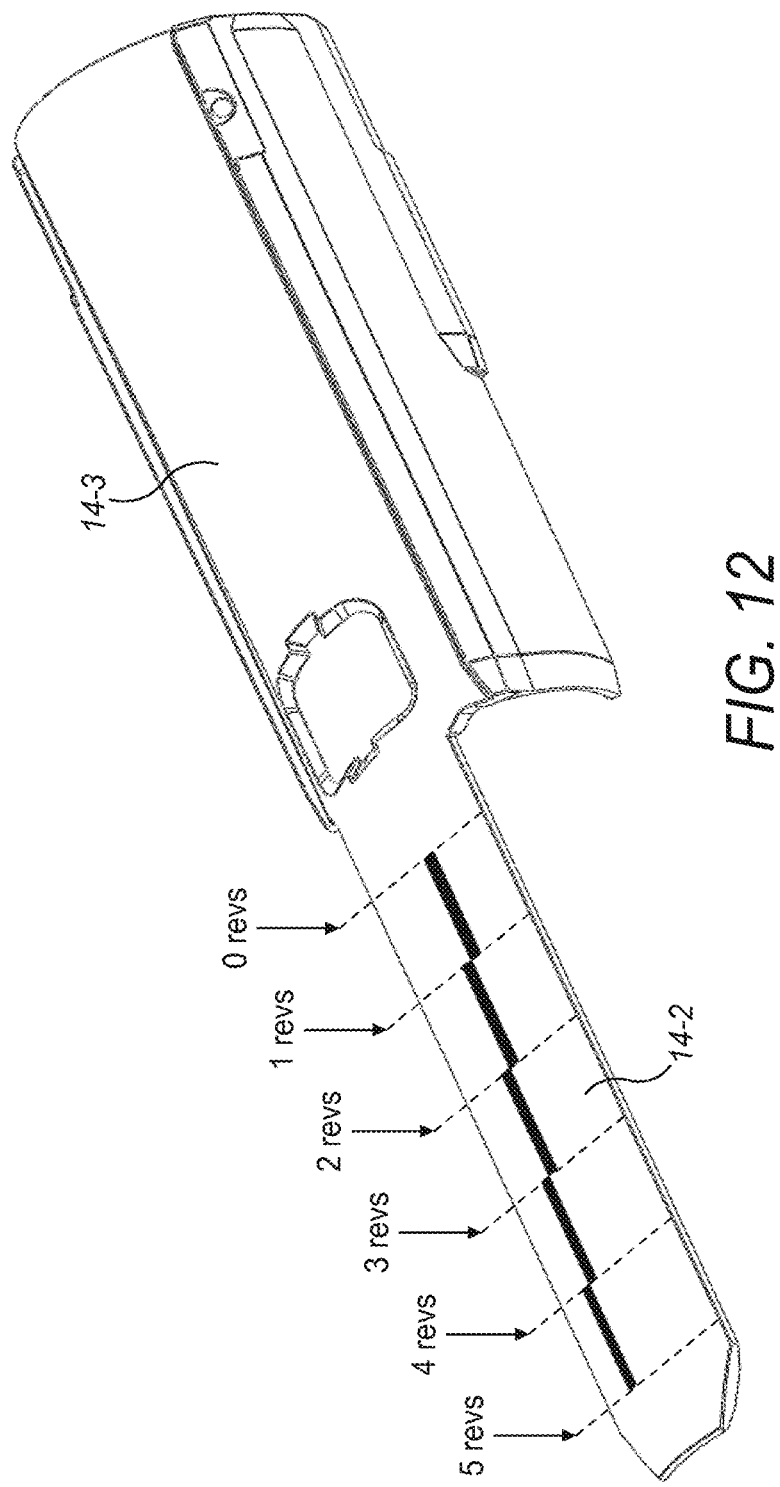
FIG. 12 is an isometric view of a gauge element of the drug delivery device.

An alternative arrangement for allowing the sensor device 2 to determine the number of rotations of the number sleeve from the initial position to the currently set dose will now be described with reference to FIG. 12. Here, the gauge element 14 includes a number of marks, which are shown in this example on the exterior surface of the second part 14-2 of the gauge element 14. The marks each extend generally parallel to the longitudinal axis of the drug delivery device 1. However, the angular position varies for different marks. In particular, each mark is at a different angular position. The marks are spaced in the axial direction. The marks are at different angular positions at different axial positions.

The marks may be provided in visible ink. They may alternatively be provided in ink which is invisible, for instance ink which is visible only in infra-red or ultra-violet. This can allow the sensing arrangement 20 to detect the marks but without potentially confusing a user of the device 1.

The sensing arrangement 20 is located so as to view the mark that is present at a certain axial position. By operating the circuitry 21 to determine the angular position of the mark, the axial position of the gauge element 14 can be determined to within the resolution of the length of the marks. By providing each of the marks with a length that corresponds to one full rotation of the number sleeve 15A, the circuitry 21 can determine the number of rotations of the number sleeve from the initial position by detecting the angular position of the mark that is viewed by the sensing arrangement 20.

Instead of lines, the marks on the gauge element may take the form of optically-readable codes, comprising encoded digital information.

Figure 11:
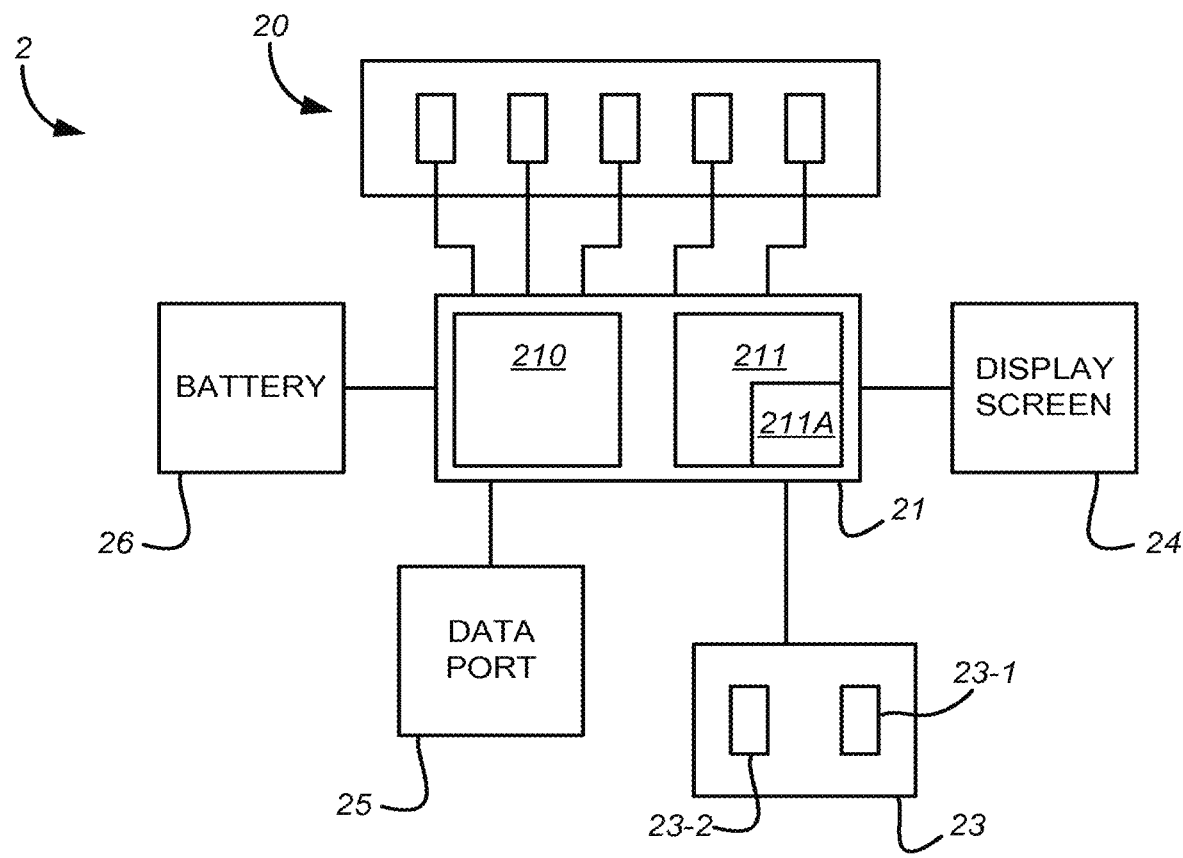
FIG. 11 is simplified block diagram of a sensor device according to embodiments of the disclosure.
Figure 13:
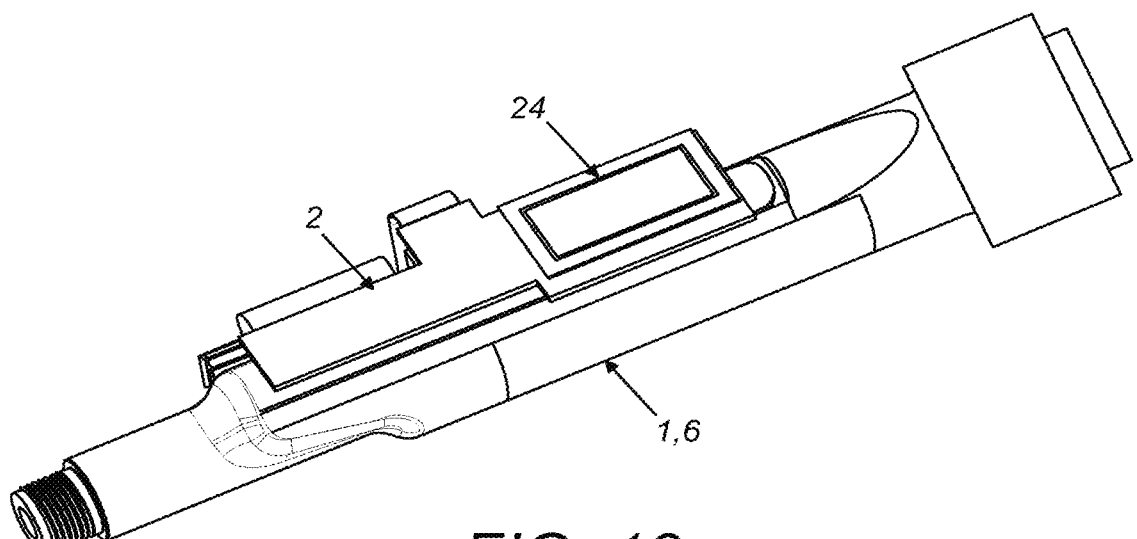
FIG. 13 shows an example of a physical arrangement of the components of the sensor device depicted in FIG. 11.

Up until now, the composition of the sensor device 2 has been described at a relatively high level. FIGS. 11, 1 and 13 depict the sensor device 2 in more detail.

FIG. 11 is a simplified schematic block diagram of a sensor device 2 according to various embodiments. As described above, the sensor device 2 comprises the array 20 of optical sensors 20-1 to 20-5 which are configured to output signals to the circuitry 21. The device 2 also comprises the further sensing arrangement 23 which is configured to output signals indicative of the encoded information to the circuitry 21.

The circuitry 21 may be of any suitable composition and may comprise any combination of one or more processors and/or microprocessors 210 (for simplicity, hereafter referred to as "the at least one processor") suitable for causing the functionality described herein to be performed. The circuitry 21 may additionally or alternatively comprise any combination of one or more hardware-only components such as ASICs, FPGAs etc. (which are not shown in FIG. 11).

The circuitry 21 may further comprise any combination of one or more non-transitory computer readable memory media 211, such as one or both of ROM and RAM, which is coupled to the at least one processor 210. The memory 211 may have computer-readable instructions 211A stored thereon. The computer readable instructions 210, when executed by the at least one processor 210 may cause the sensor device 2 to perform the functionality described in this specification, such as controlling operation of the array 20 and sensing arrangement 23 and interpreting the signals received therefrom.

The further sensing arrangement 23 comprises at least a light source 23-2 and a photosensor 23-1. The light source 23-2 is for illuminating the code 66 that is visible within the further window 63 formed in the device housing 62, and for illuminating the drive sleeve 68 if it is viewable through the further window (i.e. if not obscured by the number sleeve 15A).

The photosensor 23-1 is configured to process an image (which includes the code 66) which is visible to the photosensor (i.e. which underlies the photosensor). The image is detected by detecting the light reflected back from different parts of the surface(s) on which the image is provided. The image, including an image of the code 66, is then passed to the circuitry 21. The image is then processed by the circuitry 21 to determine the presence or absence of the drive sleeve 68, and to determine therefrom whether the drug delivery device 1 is in the dose setting mode or the dose delivery mode. The image is processed also to determine the rotational position of the number sleeve 15A.

Instead of one photosensor 23-1, separate sensors may be used for detecting the code 66 and for detecting the presence or absence of the drive sleeve 68.

The sensing arrangement 23 may comprise further non-electrical components, which are not shown on FIG. 11. These non-electrical components of the sensing arrangement 23 are described with reference to FIG. 14.

The sensor device 2 may further comprise one or both of a display screen 24 (such as an LED or LCD screen) and a data port 25. The display screen 24 may be operable under the control of the circuitry 21 to display information regarding operation of the drug delivery device 1 to the user. For instance, the dialled dose determined by the sensor device 2 may be displayed to the user. Other information which can be determined by the sensor device 2 includes the drug being dispensed, and/or a history of previously-dispensed doses.

The data port 25 may be used to transfer stored information relating to the operation of the drug delivery device 1 from the memory 211 to a remote device such a PC, tablet computer, or smartphone. Similarly, new software/firmware may be transferred to the sensor device via the data port 25. The data port 25 may be a physical port such as a USB port or may be a virtual, or wireless, port such as an IR, WiFi or Bluetooth transceiver.

The sensor device 2 may further comprise a removable or permanent (preferably rechargeable with e.g. photovoltaic cells) battery 26 for powering the other components of the device 2. Instead of the battery 26, a photovoltaic or capacitor power source may be used. Other electrical components which are not shown in FIG. 11, but which may nonetheless be included in the sensor device 2 include a trigger buffer 27-1, a regulator 27-2, a voltage suppressor 27-3 and a charger chip 27-4, for charging the rechargeable battery if present.

Figure 14:
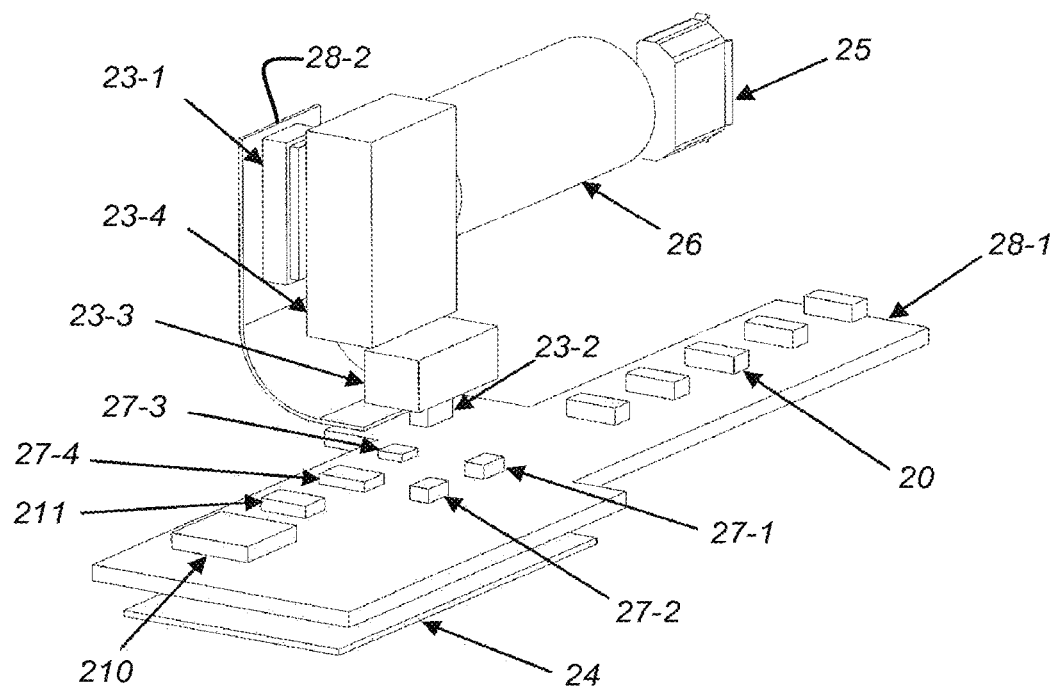
FIG. 14 shows the sensor device as depicted in FIG. 13 in situ on a drug delivery device.

FIG. 14 shows an example of a physical arrangement of the components of the sensor device of FIG. 11. The optical sensors 20-1 to 20-5 of the array 20 are arranged on a first surface of a PCB 28-1 in a way that is determined by the shape of the visible path of the movable element 14 with which the sensor device 2 is designed to be used. In the examples described herein, the visible path is linear and, consequently, the optical sensors 20-1 to 20-5 of the array 20 are linearly arranged on the PCB 28-1. When the sensor device 2 is attached to the drug delivery device 1, the first surface of the PCB 28-1 faces the at least one window 13A, 13B of the drug delivery device 1.

One or more of: the light source 23-2 of the sensor arrangement 23, the at least one processor 210, the memory 211, the charger chip 27-4, the voltage suppressor 27-3, the regulator 27-2 and the trigger buffer 27-1 may also be provided on the first surface of the PCB 28-1.

The screen or display 24 is provided on the opposite side of the PCB to the 28-1 to the array 20 of optical sensors 20-1 to 20-5, such that it is visible to the user when the sensor device 2 is attached to the drug delivery device 1. The sensor device 2 may be configured so as to extend over the entire area of the at least one window 13A, 13B such that the at least one window 13A, 13B is not visible to the user when the sensor device 2 is attached.

The photosensor 23-1 of the sensing arrangement 23 may not be provided on the PCB 28-1. Instead, the photosensor 23-1 may be provided on a support element 28-2 which extends from the PCB 28-1. In the example of FIG. 14, the support element 28-2 extends perpendicularly from the PCB, such that when it is attached to the drug delivery device 1, it wraps around a side of the device 1.

As will be appreciated the exact physical arrangement of the components within the sensor device 2 may not be crucial as long as, when the sensor device 2 is attached to the drug delivery device 1, the array 20 of optical sensors is aligned with and faces the visible path of the movable element 14. In embodiments including the further sensing arrangement 23, it may also be important that the photosensor 23-1 of the sensing arrangement 23 is positioned so as to overlie further window 63 formed in the housing 12 of the drug delivery device 1.

The sensing arrangement 23, in this example, further comprises a light guide 23-3 for guiding the light from the light source 23-2 to the further window 63 of the drug delivery device 1. The sensing arrangement 23 also comprises a lens array 23-4 for focusing on the photosensor 23-1 the light reflected back from the surface(s) underlying the photosensor 23-1. Put another way, the lens array 23-4 is configured to focus the image, which is provided on the surface(s) underlying the photosensor 23-1, on to the photosensor 23-2.

FIG. 13 shows one embodiment of the sensor device 2, without a housing, in position on the drug delivery device 1. Although not shown, the sensor device 2 may be configured to be removably attached in position on the drug delivery device 1. For instance, the housing (not shown) of the sensor device 2 may include a coupling mechanism for securely affixing the sensor device 2 to the drug delivery device 1. Alternatively, any other means for securing the sensor device 2 in position on the drug delivery device 1 may be used.

As discussed above, the code 66 that is read by the sensing arrangement 23 may include a portion of a code 66 for enabling the circuitry to determine the rotational orientation of the rotatable element 15A, 65A. However, in some embodiments, other operational information may alternatively or additionally be included in the code 66 that is read by the sensing arrangement. For instance, the code 66 may include a portion (for instance in the form of a bar code—not shown) for indicating the drug that is being delivered, in the sense of indicating the brand name or scientific name of the drug. The drug indication code portion (not shown) may be provided on, for instance, a portion of a drug cartridge that is inserted into the drug delivery device 1 and which is visible through the further window 63 and so can be read by the sensing arrangement 23. Alternatively, it may be provided on a portion of the exterior of the delivery device housing 12 that is adjacent the further window 63 and which is also beneath (and so readable by) the photosensor 23-1 of the sensing arrangement 23 when the sensor device 2 attached to the drug delivery device 1.

In some embodiments, the sensor device 2 is configured to store a history of dispensed drug doses. This may be carried out by storing information indicative of the currently dialled dose, when a change from dialling mode to delivery mode is detected based on the mode indicator 68. A timestamp indicative of a time at which the mode change occurred may also be stored in association with the information indicative of the dose. In addition or alternatively, information indicative of the type of the dispensed drug, which is determined based on the drug indication code portion 67, may be stored in association with the dose information. This may be repeated each time a dose of a drug is dispensed Information about the type of drug may be determined in any suitable way. The type of drug may be indicated on the drug delivery device 1 by printing, etching or moulding. It may instead be indicated on a printed or etched label. Such markings can be read by the sensor device optically, either in the visible spectrum or in infrared or ultra-violet. Alternatively, the type of drug may be indicated electronically, e.g. on an RFID transponder or in some other wired or wireless memory device.

Although the drug delivery devices described herein include two windows 13A, 13B through which the movable gauge element 14 is visible, it will be appreciated (particularly from the discussions of FIGS. 4A to 4D) that sensor devices 2 according to embodiments of the disclosure may be used with drug delivery devices 1 which include only one of these windows 13A, 13B.

Although a few embodiments have been shown and described, it would be appreciated by those skilled in the art that changes may be made in these embodiments without departing from the principles of the disclosure, the scope of which is defined in the claims.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. A sensor device configured to be removably attached to a drug delivery device, the sensor device comprising:
  a sensor arrangement arranged within the sensor device, the sensor arrangement including one or more sensors; and
  a circuitry configured to process signals provided by the sensor arrangement,
  wherein the sensor arrangement is configured such that, when the sensor device is attached to the drug delivery device, the sensor arrangement is operable to read encoded information present on a rotatable component that is internal to the drug delivery device and that is able to be sensed through a window or aperture of the drug delivery device, and is operable to sense through the window or aperture at least a part of a drive sleeve of the drug delivery device, and
  wherein the circuitry is configured:
    to determine, based on the encoded information, information relating to a set dose, and
    to determine, based on sensing of the part of the drive sleeve, information relating to whether the drug delivery device is in a dose setting mode or whether the drug delivery device is in a dose delivery mode.

2. The sensor device as claimed in claim 1, wherein the circuitry is configured to process signals provided by the sensor arrangement
to determine presence or absence of the drive sleeve in the window or aperture, and
to determine, based on the determined presence or absence of the drive sleeve in the window or aperture, whether the drug delivery device is in the dose setting mode or whether the drug delivery device is in the dose delivery mode.

3. The sensor device as claimed in claim 2, wherein the circuitry is configured to determine that the drug delivery device is in the dose setting mode when the part of the drive sleeve is determined to be absent in the window or aperture.

4. The sensor device as claimed in claim 2, wherein the circuitry is configured to determine that the drug delivery device is in the dose delivery mode when the part of the drive sleeve is determined to be present in the window or aperture.

5. The sensor device as claimed in claim 1, wherein the sensor arrangement is an optical sensor arrangement.

6. The sensor device as claimed in claim 5, wherein the sensor arrangement is a single camera.

7. The sensor device as claimed in claim 1, wherein the sensor arrangement comprises:
a light source arrangement configured to project light towards the aperture or window in the drug delivery device when the sensor device is attached to the drug delivery device.

8. The sensor device as claimed in claim 1, further comprising a second sensor arrangement arranged within the sensor device and configured to detect an amount of axial movement of a gauge element of the drug delivery device,
wherein the circuitry is configured to calculate the set dose using the encoded information and using outputs from the second sensor arrangement.

9. The sensor device as claimed in claim 8, wherein the second sensor arrangement comprises an array of optical sensors, each optical sensor being operable to detect light received at different locations along a linear path and to output a signal indicative of an amount of detected light.

10. The sensor device as claimed in claim 8, wherein the second sensor arrangement is configured to determine an angular position of a mark on the gauge element.

11. The sensor device as claimed in claim 8, wherein the second sensor arrangement is configured to determine a drug for which the drug delivery device is being used to dispense using the encoded information or using outputs from the second sensor arrangement.

12. A drug delivery system comprising:
a sensor device configured to be removably attachable to a drug delivery device, the sensor device comprising:
a sensor arrangement arranged within the sensor device, the sensor arrangement including at least one sensor, and
a circuitry configured to process signals provided by the sensor arrangement,
wherein the sensor arrangement is configured such that, when the sensor device is attached to the drug delivery device, the sensor arrangement is operable to read encoded information present on a rotatable component that is internal to the drug delivery device and that is able to be sensed through a window or aperture of the drug delivery device, and is operable to sense through the window or aperture at least a part of a drive sleeve of the drug delivery device, and
wherein the circuitry is configured:
to determine, based on the encoded information, information relating to a set dose, and
to determine, based on sensing of the part of the drive sleeve, information relating to whether the drug delivery device is in a dose setting mode or whether the drug delivery device is in a dose delivery mode; and the drug delivery device comprising:
a main body,
a number sleeve having markings thereon,
a dose setting mechanism configured to rotate the number sleeve without axially moving the number sleeve as a dose set is increased or decreased in the dose setting mode,
a drive mechanism configured to cause expulsion of the set dose upon application of a driving force in the dose delivery mode, and
the window located at a fixed axial position on the main body and coincident with the markings on the number sleeve,
wherein the drive sleeve of the drive mechanism is arranged to move between a first position in which the drive sleeve is coincident with the window and is visible through the window and a second position in which the drive sleeve is not visible through the window.

13. The drug delivery system as claimed in claim 12, wherein the drive sleeve is of a contrasting colour to the rotatable component.

14. The drug delivery system as claimed in claim 12 wherein the drug delivery device further comprises a gauge element that is moveable axially along an underlying element and is configured such that a movement of the gauge element in a particular direction causes the underlying element to become visible at successive locations along an externally visible path,
wherein at least part of the gauge element has a first reflectance and the underlying element has a second reflectance different from the first reflectance.

15. The drug delivery system of claim 14, wherein the gauge element is movable relative to the underlying element such that a movement in a first direction along the externally visible path causes an increasing length of the underlying element to become visible in the externally visible path.

16. The drug delivery system of claim 14, wherein the gauge element has a plurality of marks formed thereon, wherein an angular position of each mark in the plurality of marks changes as an axial position of that mark changes.

17. The drug delivery system as claimed in claim 12, wherein the drive sleeve is coincident with the window and is visible through the window when the drug delivery device is in the dose delivery mode and is not visible through the window when the drug delivery device is in the dose setting mode.

18. A drug delivery device comprising:
a main body;
a number sleeve having markings thereon;
a dose setting mechanism configured to rotate the number sleeve without axially moving the number sleeve as a dose set is increased or decreased in a dose setting mode of the drug delivery device;
a drive mechanism configured to cause expulsion of a set dose upon application of a driving force in a dose delivery mode of the drug delivery device; and
a window located at a fixed axial position on the main body and coincident with the markings on the number sleeve, wherein a drive sleeve of the drive mechanism is arranged to move between a first position in which the drive sleeve is coincident with the window and is visible through the window when the drug delivery device is in the dose delivery mode, and a second position in which the drive sleeve is not visible through the window when the drug delivery device is in the dose setting mode.

19. The drug delivery device as claimed in claim 18, further comprising a gauge element that is moveable axially along an underlying element and is configured such that a movement of the gauge element in a particular direction causes the underlying element to become visible at successive locations along an externally visible path,
   wherein at least part of the gauge element has a first reflectance and the underlying element has a second reflectance different from the first reflectance.

20. The drug delivery device as claimed in claim 19, wherein the gauge element has a plurality of marks formed thereon, wherein an angular position of each mark in the plurality of marks changes as an axial position of that mark changes.

\* \* \* \* \*